(12) United States Patent
D'Hondt et al.

(10) Patent No.: US 9,636,394 B2
(45) Date of Patent: May 2, 2017

(54) PROCESS FOR PRODUCING INFLUENZA VACCINE

(75) Inventors: Erik Jozef D'Hondt, Rixensart (BE); Hans Bernd Engelmann, Dresden (DE)

(73) Assignees: GLAXOSMITHKLINE BIOLOGICALS SA, Rixensart (BE); GLAXOSMITHKLINE BIOLOGICALS, NIEDERLASSUNG DER SMITHKLINE BEECHAM PHARMA GMBH & CO KG., Dresden (DE)

( * ) Notice: Subject to any disclaimer, the term of this patent is extended or adjusted under 35 U.S.C. 154(b) by 252 days.

(21) Appl. No.: 13/503,859

(22) PCT Filed: Oct. 25, 2010

(86) PCT No.: PCT/EP2010/066083
§ 371 (c)(1),
(2), (4) Date: Apr. 25, 2012

(87) PCT Pub. No.: WO2011/051235
PCT Pub. Date: May 5, 2011

(65) Prior Publication Data
US 2012/0219587 A1    Aug. 30, 2012

Related U.S. Application Data

(60) Provisional application No. 61/329,230, filed on Apr. 29, 2010.

(30) Foreign Application Priority Data

Oct. 27, 2009    (GB) .................................. 0918830.1

(51) Int. Cl.
*A61K 39/145* (2006.01)
*C12N 7/00* (2006.01)
*A61K 39/12* (2006.01)
*A61K 39/00* (2006.01)

(52) U.S. Cl.
CPC ............ *A61K 39/145* (2013.01); *A61K 39/12* (2013.01); *C12N 7/00* (2013.01); *A61K 2039/55566* (2013.01); *C12N 2760/16134* (2013.01); *C12N 2760/16151* (2013.01)

(58) Field of Classification Search
None
See application file for complete search history.

(56) References Cited

U.S. PATENT DOCUMENTS 5,650,155 A    7/1997    Cornelius et al.
5,667,784 A    9/1997    Cornelius et al.

FOREIGN PATENT DOCUMENTS

| DE | 155875 | | 7/1983 |
|---|---|---|---|
| EP | 0382271 B1 | | 1/1990 |
| WO | WO 95/17210 | | 6/1995 |
| WO | WO 02/097072 | * | 12/2002 |
| WO | WO 02/097072 A2 | | 12/2002 |
| WO | WO 03/076601 | | 9/2003 |
| WO | WO 2006/100109 | | 9/2006 |
| WO | WO 2008/129058 | | 10/2008 |
| WO | WO 2009/029695 | * | 3/2009 |
| WO | WO 2009/029695 A1 | | 3/2009 |
| WO | WO 2009/115917 | | 9/2009 |

OTHER PUBLICATIONS

Beyer, et al., "Comparison of serology and reactogenicity between influenza subunit vaccines and whole virus or split vaccines. A review and meta-analysis of the literature", Clin Drug Invest., 15:1-12, 1998.
Crabb, et al., "The determination of polyoxyethylene nonionic surfactants in water at the parts per million level", J. Amer. Oil Chem. Soc., 41:752-755, 1964.
EMA/CHMP/BWP/214/96, Committee for Proprietary Medicinal Products (CPMP)."Note for harmonization of requirements for influenza vaccines", 1997.
EMA/CHMP/VWP/263499/2006, "Guideline on influenza vaccines prepared from viruses with the potential to cause a pandemic and intended for use outside of the core dossier context", 2007.
EMA/CHMP/VWP/40560/2014, "Explanatory note on the withdrawal of the Note for guidance on harmonisation of requirements for influenza vaccines and of the core SmPC/PL for inactivated seasonal influenza vaccines", 2014.
Fouchier, et al., Characterization of a Novel Influenza A Virus Hemagglutinin Subtype (H16) Obtained from Black-Headed Gulls, J. Virol., 79:2814-2822, 2005.
Greff, et al., "A colorimetric method for the determination of parts/million of nonionic surfactants", J. Amer. Oil Chem. Soc., 42:180-185, 1965.
Lina, et al, "A TritonX-100-split virion influenza vaccine is safe and fulfils the committee for propriety medicinal products (CPMP) recommendations for the European Community for Immunogenicity, in children adults and the elderly", Biologicals 28:95-103, 2000.
Webster, et al., "Evolution and ecology of influenza A viruses", Microbiol.Rev., 56:152-179, 1992.
Wood et al., International collaborative study of single radial diffusion and immunoelectrophoresis techniques for the assay of haemagglutinin antigen of influenza virus, J. Biol. Stand. 9:317-330, 1981.
Wood, et al., "An improved single radial immunodiffusion technique for the assay of influenza haemagglutinin antigen: Adaptation for potency determination of inactivated whole virus and subunit vaccines", J. Biol. Stand., 5:237-247, 1977.

* cited by examiner

*Primary Examiner* — Shanon A Foley
*Assistant Examiner* — Myron Hill
(74) *Attorney, Agent, or Firm* — Natalie A. Lissy

(57) ABSTRACT

A process for producing a split influenza virus preparation or subunit influenza preparation comprising the steps of: (i) providing a whole virus preparation; (ii) splitting the whole virus preparation in the presence of a first detergent; (iii) adding t-octylphenoxypolyethoxyethanol (TRITON X-100™) to the resulting split virus preparation; and (iv) filtering the split virus preparation.

18 Claims, 9 Drawing Sheets

FIG.1

| H1N1V PROCESS A | H1N1V PROCESS A + T-OCTYLPHENOXYPOLYETHOXYETHANOL (TRITON X-100™) | MODIFIED "FLUARIX" APPROVED PROCESS FOR SEASONAL INFLUENZA + T-OCTYLPHENOXYPOLYETHOXYETHANOL (TRITON X-100™) |
|---|---|---|
| 1 CRUDE MONOVALENT WHOLE VIRUS BULK<br>2 CLARIFICATION<br>3/1 ULTRAFILTRATION I<br>4 FLOW THROUGH ULTRACENTRIFUGATION<br>6 PURIFIED MONOVALENT WHOLE VIRUS BULK<br>7 FLOW THROUGH ULTRACENTRIFUGATION VIRUS SPLITTING IN SODIUM DEOXYCHOLATE<br>7/2 FRACTION SELECTION<br>8/1 PURIFIED MONOVALENT SPLIT VIRUS BULK<br>8/2+ 8/3 GRADUAL FILTRATION<br>8/4 INACTIVATION<br>8/5+ 8/6 ULTRAFILTRATION II<br>8/7 GRADUAL FILTRATION + STERILE FILTRATION<br>9 PURIFIED MONOVALENT INACTIVATED, STERILE SPLIT VIRUS BULK | 1 CRUDE MONOVALENT WHOLE VIRUS BULK<br>2 CLARIFICATION<br>3/1 ULTRAFILTRATION I<br>4 FLOW THROUGH ULTRACENTRIFUGATION<br>6 PURIFIED MONOVALENT WHOLE VIRUS BULK<br>7 FLOW THROUGH ULTRACENTRIFUGATION VIRUS SPLITTING IN SODIUM DEOXYCHOLATE<br>7/2 FRACTION SELECTION<br>8/1 PURIFIED MONOVALENT SPLIT VIRUS BULK<br>8/2+ 8/3 GRADUAL FILTRATION<br>T-OCTYLPHENOXYPOLYETHOXYETHANOL (TRITON X-100™) ADDED<br>8/4 INACTIVATION<br>8/5+ 8/6 ULTRAFILTRATION II<br>8/7 GRADUAL FILTRATION + STERILE FILTRATION<br>9 PURIFIED MONOVALENT INACTIVATED, STERILE SPLIT VIRUS BULK | 1 CRUDE MONOVALENT WHOLE VIRUS BULK<br>2 CLARIFICATION<br>3/1 ULTRAFILTRATION I<br>4 FLOW THROUGH ULTRACENTRIFUGATION<br>6 PURIFIED MONOVALENT WHOLE VIRUS BULK<br>7 FLOW THROUGH ULTRACENTRIFUGATION VIRUS SPLITTING IN SODIUM DEOXYCHOLATE<br>7/2 FRACTION SELECTION<br>8/1 PURIFIED MONOVALENT SPLIT VIRUS BULK<br>8/2+ 8/3 GRADUAL FILTRATION<br>T-OCTYLPHENOXYPOLYETHOXYETHANOL (TRITON X-100™) ADDED<br>8/4 INACTIVATION<br>8/5+ 8/6 ULTRAFILTRATION II<br>8/7 GRADUAL FILTRATION + STERILE FILTRATION<br>9 PURIFIED MONOVALENT INACTIVATED, STERILE SPLIT VIRUS BULK |

FIG.2    Average HA content of three lots of Pandemic H1N1strain/California/7/2009
         NYMC X-179A (AFLSIDA046, 048, 050) as measured by HPLC after several
         process steps

FIG.3 SDS-PAGE of H1N1v monovalent bulk produced with/without addition of t-octylphenoxypolyethoxyethanol (TRITON X-100™)

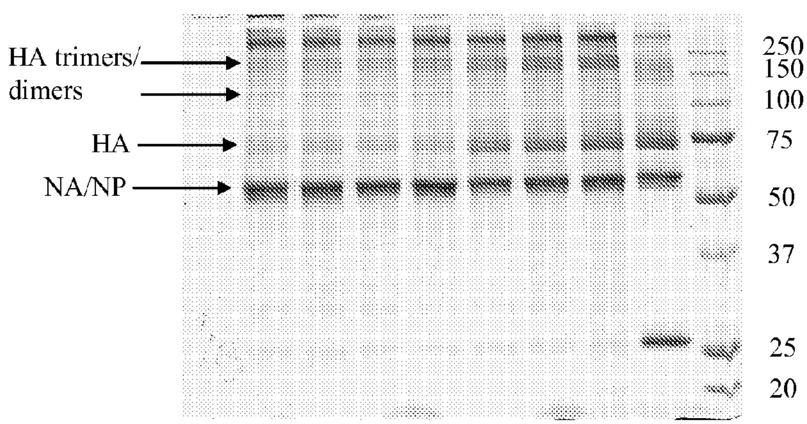

| Lane | Sample (Production step 9: purified monovalent inactivated, sterile split virus bulK) |
|---|---|
| 2 | AFLSFDA068 Step 9 |
| 3 | AFLSFDA070 Step 9 |
| 4 | AFLSFDA072 Step 9 |
| 5 | AFLSIDA083 Step 9 |
| 6 | DFLSIDA028 Step 9 (t-octylphenoxypolyethoxyethanol (TRITON X-100™) lot) |
| 7 | DFLSIDA029 Step 9 (t-ctylphenoxypolyethoxyethanol (TRITON X-100™) lot) |
| 8 | DFLSIDA027 Step 9 (t-octylphenoxypolyethoxyethanol (TRITON X-100™) lot) |
| 9 | HA Standard A/Calif/7/2009 TGA |
| 10 | Molecular Weight Marker |

FIG. 4    HI titers (GMT +/- CI95) on Day 14 Post-II in BALB/c mice immunised with the non-adjuvanted A/California/7/2009 split vaccine prepared without addition of t-octylphenoxypolyethoxyethanol (TRITON X-100™)
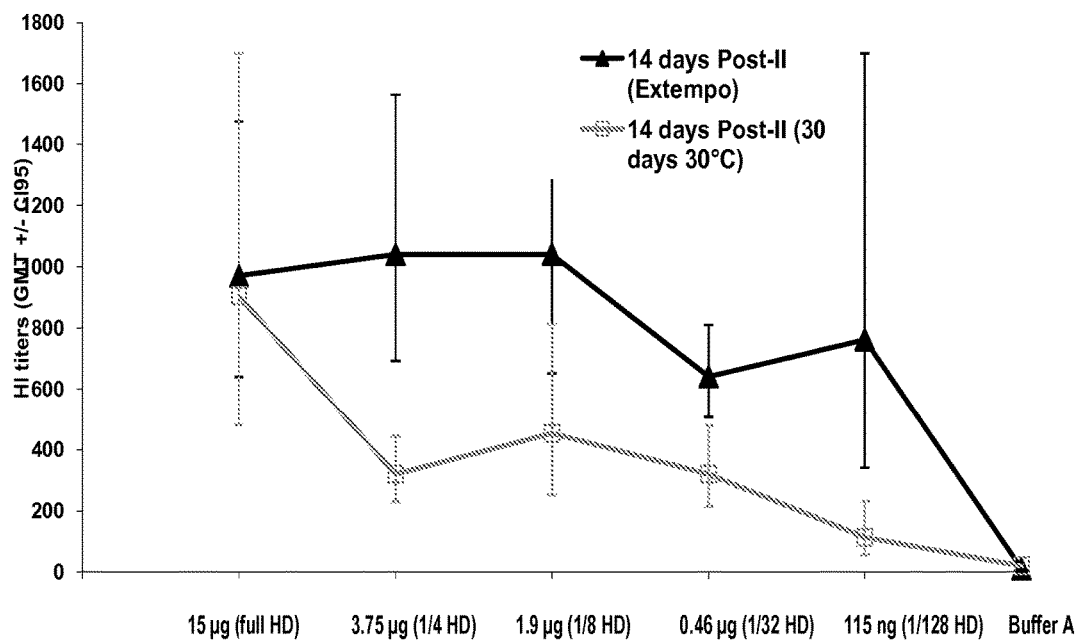

FIG. 5  HI titers (GMT +/- CI95) on day 14 Post-II in BALB/c mice immunized with the non-adjuvanted A/California/7/2009 split vaccine prepared with the addition of t-octylphenoxypolyethoxyethanol (TRITON X-100™)
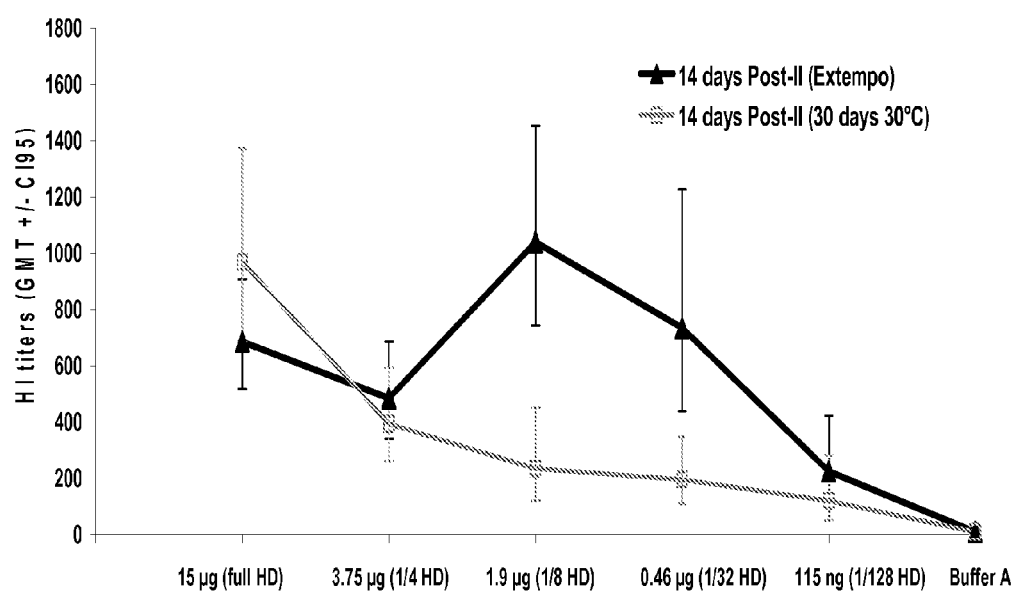

FIG.6 HI titres (GMT +/- CI95) in BALB/c mice for AS03A adjuvanted vaccine A/California/7/2009 NYMC X-179A without additional t-octylphenoxypolyethoxyethanol (TRITON X-100™) -14PI
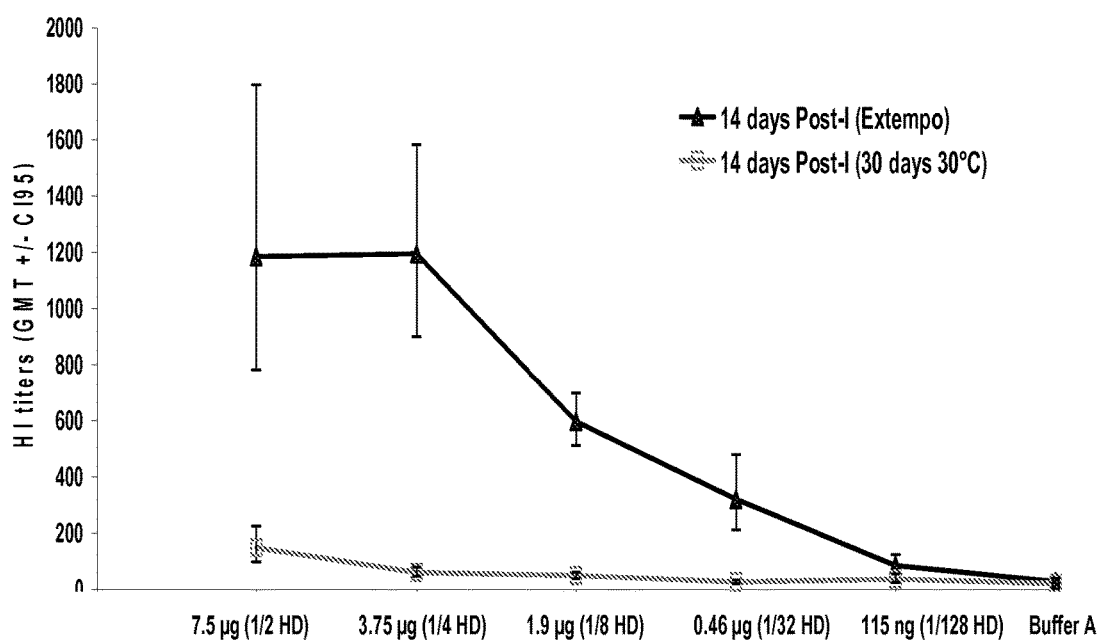

FIG.7  Inhibition of hemagglutination titres (GMT +/- CI95) in BALB/c mice for AS03A adjuvanted vaccine A/California/7/2009 NYMC X-179A with additional t-octylphenoxypolyethoxyethanol (TRITON X-100™) -

FIG.8    Inhibition of hemagglutination titres (GMT +/- CI95) in BALB/c mice for AS03A adjuvanted vaccine A/California/7/2009 NYMC X-179A without additional t-octylphenoxypolyethoxyethanol (TRITON X-100™) -14PII
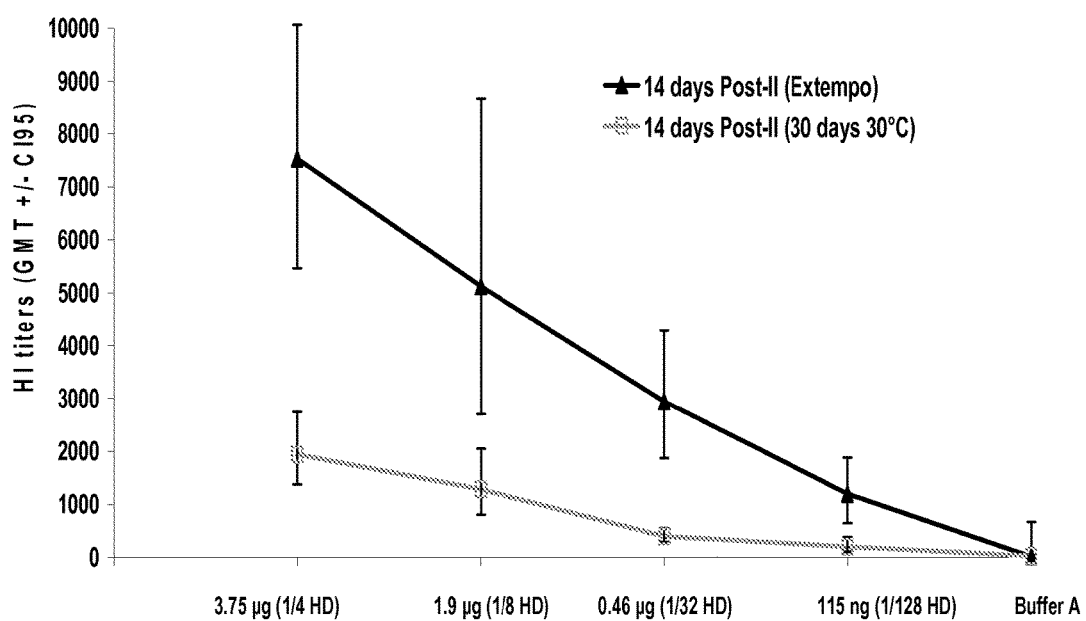

FIG. 9  Inhibition of hemagglutination titres (GMT +/- CI95) in BALB/c mice for AS03A adjuvanted vaccine A/California/7/2009 NYMC X-179A with additional t-octylphenoxypolyethoxyethanol (TRITON X-100™) -14PII
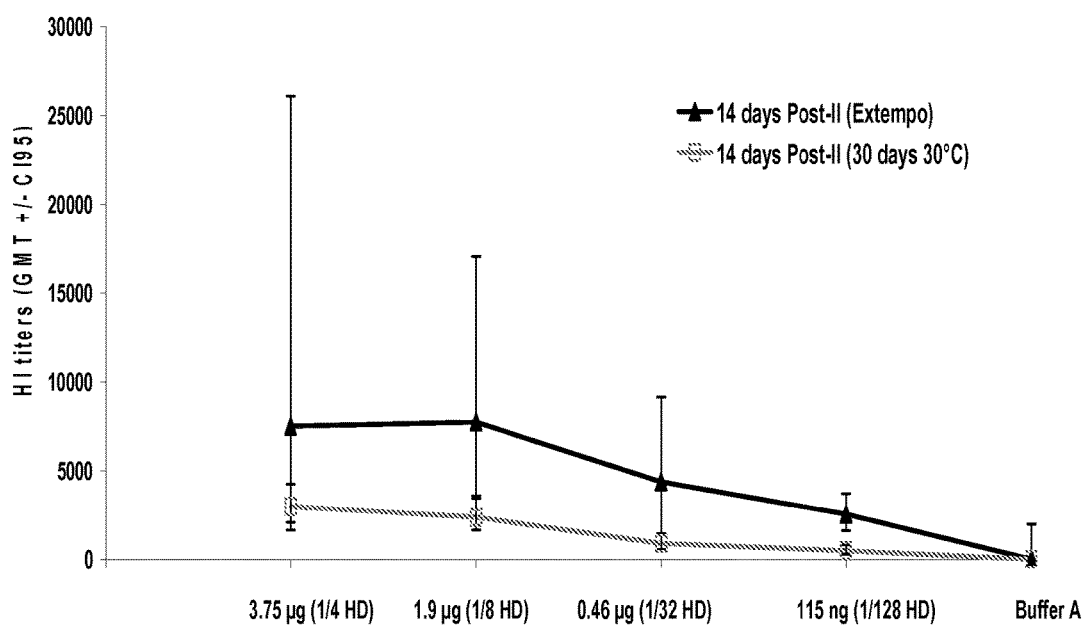

PROCESS FOR PRODUCING INFLUENZA VACCINE

CROSS-REFERENCE TO RELATED APPLICATIONS

This application is the US National Stage of International Application No. PCT/EP2010/066083, filed 25 Oct. 2010, which claims benefit of priority to U.S. Provisional Application No. 61/329,230, filed 29 Apr. 2010, which applications are incorporated herein by reference in their entirety. This application also claims benefit of the filing date of GB 0918830.1, filed 27 Oct. 2009.

COPYRIGHT NOTIFICATION PURSUANT TO 37 C.F.R. §1.71(E)

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Field of the Invention

The present invention relates to process for making influenza antigens suitable for use in vaccines and pharmaceutical compositions comprising said antigens.

Description of the Related Background

Influenza viruses are one of the most ubiquitous viruses present in the world, affecting both humans and livestock. Influenza results in an economic burden, morbidity and even mortality, which are significant.

The influenza virus is an RNA enveloped virus with a particle size of about 125 nm in diameter. It consists basically of an internal nucleocapsid or core of ribonucleic acid (RNA) associated with nucleoprotein, surrounded by a viral envelope with a lipid bilayer structure and external glycoproteins. The inner layer of the viral envelope is composed predominantly of matrix proteins and the outer layer mostly of host-derived lipid material. Influenza virus comprises two surface antigens, glycoproteins neuraminidase (NA) and haemagglutinin (HA), which appear as spikes, 10 to 12 nm long, at the surface of the particles. It is these surface proteins, particularly the haemagglutinin that determine the antigenic specificity of the influenza subtypes. Virus strains are classified according to host species of origin, geographic site and year of isolation, serial number, and, for influenza A, by serological properties of subtypes of HA and NA. 16 HA subtypes (HI-HI 6) and nine NA subtypes (N1-N9) have been identified for influenza A viruses [Webster R G et al. Evolution and ecology of influenza A viruses. Microbiol. Rev. 1992; 56:152-179; Fouchier R A et al. Characterization of a Novel Influenza A Virus Haemagglutinin Subtype (H16) Obtained from Black-Headed Gulls. J. Virol. 2005; 79:2814-2822). Viruses of all HA and NA subtypes have been recovered from aquatic birds, but only three HA subtypes (H1, H2, and H3) and two NA subtypes (N1 and N2) have established stable lineages in the human population since 1918. Only one subtype of HA and one of NA are recognised for influenza B viruses.

At unpredictable intervals, novel influenza viruses emerge with the haemagglutinin antigen, of a totally different subtype from strains circulating the season before. Here, the resulting antigens can vary from 20% to 50% from the corresponding protein of strains that were previously circulating in humans. This phenomenon, called "antigenic shift" can result in virus escaping 'herd immunity' and establishing pandemics. In other words, an influenza pandemic occurs when a new influenza virus appears against which the human population has no immunity.

During a pandemic, antiviral drugs may not be sufficient or effective to cover the needs and the number of individuals at risk of influenza will be greater than in interpandemic periods, therefore the development of a suitable vaccine with the potential to be produced in large amounts and with efficient distribution and administration potential is essential. Improved processes are also important to maximize production of antigen for seasonal (interpandemic) influenza vaccines, as the population generally ages and the need for influenza vaccines increases.

The present invention addresses this need.

SUMMARY OF THE INVENTION

In a first aspect the present invention provides a process for producing a split influenza virus or a subunit influenza preparation comprising the steps of: (i) providing a whole virus preparation; (ii) splitting the whole virus preparation in the presence of a first detergent; (iii) adding t-octylphenoxypolyethoxyethanol (TRITON X-100™) to the resulting split virus preparation; and (iv) filtering the split virus preparation.

The invention also relates to a split influenza virus preparations and/or subunit influenza virus preparations obtained or obtainable by said process.

The invention also relates to a process for preparing a pharmaceutical or immunogenic composition, comprising the steps of: (i) providing a split influenza virus or a subunit influenza preparation produced by a process of the invention as described herein, (ii) admixing said a split influenza virus or a subunit influenza preparation with a pharmaceutically acceptable carrier to prepare pharmaceutical or immunogenic composition.

The invention also relates to a pharmaceutical or immunogenic composition obtained or obtainable by a process of the invention.

The invention also relates to a method of inducing an immune response in a human subject, said method comprising administering to the subject said pharmaceutical or immunogenic composition as described herein.

The invention further relates to a pharmaceutical and/or immunogenic composition as defined herein for use in the treatment or prevention of influenza disease or infection.

The invention also relates to an antigen preparation comprising an influenza virus hemagglutinin (HA) and a detergent wherein the weight ratio of detergent (µg/ml) to hemagglutinin (µg/ml) is between 1.5 and 15.

The invention also relates to a process for producing a split influenza virus or subunit influenza preparation comprising the steps of: (i) providing a whole influenza virus preparation, (ii) splitting the whole virus preparation in the presence of a detergent added in an amount suitable to prevent aggregation of viral particles once split.

The invention also relates to a vaccine comprising one or more split influenza virus preparations or subunit influenza preparations prepared according to any of the processes described herein.

BRIEF DESCRIPTION OF THE DRAWINGS

FIG. 1 discloses various influenza vaccine production processes.

FIG. 2 discloses the loss of HA after several production steps without the addition of t-octylphenoxypolyethoxyethanol (TRITON X-100™) 8/1: purified monovalent split virus bulk; 8/2 and 8/3: gradual filtration; 8/4: Inactivation.

FIG. 3 discloses SDS-PAGE of H1N1v monovalent bulk produced with/without addition of t-octylphenoxypolyethoxyethanol (TRITON X-100™).

FIG. 4 discloses HI titers (GMT+/−CI95) on Day 14 Post-II in BALB/c mice immunised with the non-adjuvanted A/California/7/2009 split vaccine prepared without addition of t-octylphenoxypolyethoxyethanol (TRITON X-100™).

FIG. 5 discloses HI titers (GMT+/−CI95) on day 14 Post-II in BALB/c mice immunized with the non-adjuvanted A/California/7/2009 split vaccine prepared with the addition of t-octylphenoxypolyethoxyethanol (TRITON X-100™).

FIG. 6 discloses HI titres (GMT+/−CI95) in BALB/c mice for AS03A adjuvanted vaccine A/California/7/2009 NYMC X-179A without additional t-octylphenoxypolyethoxyethanol (TRITON X-100™)-14PI.

FIG. 7 discloses inhibition of hemagglutination titres (GMT+/−CI95) in BALB/c mice for AS03A adjuvanted vaccine A/California/7/2009 NYMC X-179A with additional t-octylphenoxypolyethoxyethanol (TRITON X-100™)-14PI.

FIG. 8 discloses inhibition of hemagglutination titres (GMT+/−CI95) in BALB/c mice for AS03A adjuvanted vaccine A/California/7/2009 NYMC X-179A without additional t-octylphenoxypolyethoxyethanol (TRITON X-100™)-14PII.

FIG. 9 discloses Inhibition of hemagglutination titres (GMT+/−CI95) in BALB/c mice for AS03A adjuvanted vaccine A/California/7/2009 NYMC X-179A with additional t-octylphenoxypolyethoxyethanol (TRITON X-100™)-14PII.

DETAILED DESCRIPTION

The inventors have determined that the use of t-octylphenoxypolyethoxyethanol (TRITON X-100™) in combination with a split virus preparation increases in the yield of antigenic components of the virus preparation. The process increases the yield of antigen from pandemic strains and seasonal (interpandemic) strains. Increased yield is desirable, e.g. because it allows for the production of a greater number of vaccine doses at a time when such vaccine doses are currently insufficient.

The use of t-octylphenoxypolyethoxyethanol (TRITON X-100™) in combination with a split virus preparation or subunit preparation also improves the purity of influenza antigens, e.g. HA or NA.

Without wishing to be bound by theory, the use of t-octylphenoxypolyethoxyethanol (TRITON X-100™) in combination with a split influenza virus preparation helps prevent aggregation of the split viral particles and allows the influenza vaccine to be more easily filtered, which accounts in whole or in part for the increased yield observed when using t-octylphenoxypolyethoxyethanol (TRITON X-100™).

The present invention relates generally to processes for producing a split influenza virus or a subunit influenza preparation comprising the steps of: (i) providing a whole virus preparation, (ii) splitting the whole virus preparation in the presence of a first detergent, (iii) adding t-octylphenoxypolyethoxyethanol (TRITON X-100™) to the resulting split virus preparation; and (iv) filtering the split virus preparation In another aspect, the present invention provides a process for producing a split influenza virus preparation or a subunit influenza preparation comprising the steps of: (i) providing a whole virus preparation; (ii) splitting the whole virus preparation in the presence of a first detergent and (iii) adding t-octylphenoxypolyethoxyethanol (TRITON X-100™) to the resulting split virus preparation; and (iv) filtering the split virus preparation, wherein the second detergent is used in step (iii) at a concentration of at least 0.1% (v/v).

The process may comprise a further step of inactivating said split influenza virus preparation or subunit influenza preparation, suitably after step (iii).

Accordingly in a third aspect, the present invention provides a process for producing a split influenza virus preparation or a subunit influenza preparation comprising the steps of: (i) providing a whole virus preparation, (ii) splitting the whole virus preparation in the presence of a detergent; (iii) adding t-octylphenoxypolyethoxyethanol (TRITON X-100™) to the resulting split virus preparation; (iv) inactivating said split virus preparation; and (v) filtering the split virus preparation

Detergents

Split influenza virus preparations have previously been produced using a solvent/detergent treatment, such as tri-n-butyl phosphate, or diethylether in combination with polyoxyethylene sorbitan monooleate (TWEEN-80™, or POLYSORBATE 80™) (known as "Tween-ether" splitting) and this process is still used in some production facilities. Other splitting agents now employed include detergents or proteolytic enzymes or bile salts, for example sodium deoxycholate as described in patent no. DD 155 875 or in or in WO 02/097072 (U.S. Pat. No. 7,316,813B2), incorporated herein by reference. Detergents that can be used as splitting agents include cationic detergents e.g. cetyl trimethyl ammonium bromide (CTAB), other ionic detergents e.g. laurylsulfate, taurodeoxycholate, or non-ionic detergents such as the ones described above including t-octylphenoxypolyethoxyethanol (TRITON X-100™) (for example in a process described in Lina et al, 2000, Biologicals 28, 95-103) and Triton N-101, or combinations of any two or more detergents.

In one aspect the first detergent is selected from the group of: an ionic detergent such as an anionic or cationic detergent, a non-ionic detergent, a zwittergent or a combination thereof. Examples of suitable detergents are sodium deoxycholate, CTAB and t-octylphenoxypolyethoxyethanol (TRITON X-100™).

The first detergent may also be used in combination with other detergents, such as those listed above, and may be a combination of non ionic detergents, for example a combination of sodium deoxycholate and polyoxyethylene sorbitan monooleate (TWEEN-80™ or POLYSORBATE 80™) or sodium deoxycholate and t-octylphenoxypolyethoxyethanol (TRITON X-100™).

In one aspect the first is not t-octylphenoxypolyethoxyethanol (TRITON X-100™). In a specific embodiment, residual amounts of the first detergent and t-octylphenoxypolyethoxyethanol (TRITON X-100™) are present in the final split influenza or subunit antigen preparation.

In a particular embodiment of the invention the first detergent is t-octylphenoxypolyethoxyethanol (TRITON X-100™).

In an alternative embodiment of the invention, the first detergent is sodium deoxycholate.

Synonyms for t-octylphenoxypolyethoxyethanol (TRITON X-100™) include but are limited to polyethylene glycol p-(1,1,3,3-tetramethylbutyl)-phenyl ether, octyl phenol ethoxylate, polyoxyethylene octyl phenyl ether, 4-octylphenol polyethoxylate, Mono 30, TX-100, Octoxynol-9, octoxynol 10, X-100, and octylphenol ethylene oxide condensate.

In one aspect t-octylphenoxypolyethoxyethanol (TRITON X-100™) is used in combination with other detergents, such as those listed above (for example polyoxyethylene sorbitan monooleate (TWEEN-80™, or POLYSORBATE 80™), such as an ionic detergent such as an anionic or cationic detergent, a non-ionic detergent, a zwittergent or a combination thereof.

The t-octylphenoxypolyethoxyethanol (TRITON X-100™) may be added before or during filtration of the split influenza preparation so as to improve filtration. Accordingly, in one embodiment of the invention there is provided a process for producing a split influenza virus or a subunit influenza preparation comprising the steps of: (i) providing a whole virus preparation; (ii) splitting the whole virus preparation in the presence of a first detergent; (iii) adding t-octylphenoxypolyethoxyethanol (TRITON X-100™) to the resulting split virus preparation; and (iv) filtering the split virus preparation, wherein steps (iii) and (iv) are performed simultaneously.

The t-octylphenoxypolyethoxyethanol (TRITON X-100™) added to split influenza virus preparation is in an amount suitable to improve HA yield compared to a process without detergent treatment after splitting. Improved HA is suitably assessed in comparison to the results obtained without detergent treatment after splitting, for example as measured by an SRD assay on [HA] after filtration through a 0.2 µm membrane (J. M. Wood et al.: An improved single radial immunodiffusion technique for the assay of influenza haemagglutinin antigen: adaptation for potency determination of inactivated whole virus and subunit vaccines. J. Biol. Stand. 5 (1977) 237-247; J. M. Wood et al., International collaborative study of single radial diffusion and immuno-electrophoresis techniques for the assay of haemagglutinin antigen of influenza virus. J. Biol. Stand. 9 (1981) 317-330).

Accordingly, in one embodiment there is provided processes of the invention wherein t-octylphenoxypolyethoxyethanol (TRITON X-100™) is present in an amount sufficient to improve HA yield in the filtered split virus preparation.

In a particular embodiment, there is provided processes of the invention wherein the HA concentration in the filtered split influenza virus preparation or subunit preparation is more than 50%, 75%, 100%, 150%, 200% or 250% greater the HA compared to a process wherein t-octylphenoxypolyethoxyethanol (TRITON X-100™) is not added to the split virus preparation prior to filtration.

In a particular embodiment t-octylphenoxypolyethoxyethanol (TRITON X-100™) is present in an amount greater than 0.025% (w/v). In a particular embodiment t-octylphenoxypolyethoxyethanol (TRITON X-100™) is present in an amount of 0.1-1.5%. In further embodiments, t-octylphenoxypolyethoxyethanol (TRITON X-100™) is present in an amount of 0.1 to 0.8%. In yet a further embodiment, t-octylphenoxypolyethoxyethanol (TRITON X-100™) is present in an amount of 0.1 to 0.4%, e.g. 0.25% (w/v).

In one aspect the process of the invention comprises a filtration step prior to an inactivation step, suitably substantially immediately prior to inactivation, and t-octylphenoxypolyethoxyethanol (TRITON X-100™) is added before or during that filtration step.

The present invention thus relates in one aspect to a process for producing a split or subunit influenza virus preparation comprising the steps of: (i) providing a whole virus preparation, (ii) splitting the whole virus preparation in the presence of a first detergent, (iii) adding t-octylphenoxypolyethoxyethanol (TRITON X-100™) to the resulting split virus preparation, (iv) filtering of the preparation, and (v) inactivating said filtered split virus preparation.

In an alternative embodiment of the invention there is provided a process for producing a split or subunit influenza virus preparation comprising the steps of: (i) providing a whole virus preparation, (ii) splitting the whole virus preparation in the presence of a first detergent, (iii) adding t-octylphenoxypolyethoxyethanol (TRITON X-100™) to the resulting split virus preparation, and (iv) filtering the inactivated split virus preparation, further comprising the step of inactivating the split virus preparation after step (iii) and before step (iv).

Suitably filtration is carried out through a filter ≤0.45 µm, such as 0.2 µm or 0.22 µm. In one aspect the filtration is preceded by a prefiltration step. In one aspect the prefiltered product is sonicated to facilitate the filtration step.

In one aspect t-octylphenoxypolyethoxyethanol is present during the splitting process i.e. t-octylphenoxypolyethoxyethanol (TRITON X-100™) is present in addition to the first detergent.

In one aspect t-octylphenoxypolyethoxyethanol is present during splitting in an amount sufficient to prevent aggregation of viral particles once split, suitably as determined by efficacy of filtration of the split virus preparation, for example as determined by HA concentration after filtration.

An alternative aspect of the invention comprises a process for producing a split influenza virus or subunit influenza preparation comprising the steps of: (i) providing a whole virus preparation, (ii) splitting the whole virus preparation in the presence of t-octylphenoxypolyethoxyethanol (TRITON X-100™) added in an amount suitable to prevent loss of yield of HA after filtration, where loss of yield is determined as compared to a process without such a detergent being present.

In this aspect t-octylphenoxypolyethoxyethanol (TRITON X-100™) is present during splitting to improve yield of HA. Use of t-octylphenoxypolyethoxyethanol (TRITON X-100™) after splitting may not be required. The t-octylphenoxypolyethoxyethanol (TRITON X100™) may help in the splitting process, but this is not essential. Suitably t-octylphenoxypolyethoxyethanol (TRITON X-100™) is able to help reduce the loss of HA that is manifested when the preparation is filtered.

Accordingly, in one embodiment there is provided processes of the invention wherein steps (ii) and (iii) are performed simultaneously.

Influenza Strains

The whole, subunit or split influenza virus preparations as described herein, may be derived from any influenza strain.

In one embodiment of the invention whole, subunit or split influenza virus preparations as described herein is derived from an influenza A or influenza B strain. In one aspect influenza A virus strain is of a H1, H3, H7, H9 or H5 hemagglutinin sub-type. In one aspect the virus is a pandemic or a potentially pandemic (e.g. H1N1v or H5N1) strain or a non pandemic (inter-pandemic) (e.g. H3N2) strain. Data is provided herein showing the advantages of the present invention on both a pandemic (H1N1v such as A/California/7/2009 X-179A) and inter-pandemic H3N2 strains.

Suitable strains from which the whole, subunit or split influenza virus preparations of the invention are derived, include, but are not limited to:

H1N1 Strains

A/New Caledonia/20/99-like strain, A/New Caledonia/20/99 (IVR-116), A/Solomon Islands/3/2006-like virus, A/Solomon Islands/3/2006 (IVR-145), A/Brisbane/59/2007-like virus, A/Brisbane/59/2007 IVR-148, A/Singapore/6/86-like, A/Singapore/6/86, A/Texas/36/91, A/Bayern/7/95-like, A/Johannesburg/82/96 (NIB-39), A/Beijing/262/95-like, A/Beijing/262/95 (X-127), A/New Caledonia/20/99-like, A/New Caledonia/20/99 (IVR-116), A/Solomon Islands/3/2006-like, A/Solomon Islands/3/2006 (IVR-145), A/Brisbane/59/2007-like virus, A/Brisbane/59/2007 IVR-148

H3N2 Strains

A/Sydney/5/97-like strain, A/Sydney/5/97 (IVR-108), A/Moscow/10/99-like strain, A/Panama/2007/99 (RESVIR-17), A/Fujian/411/2002-like strain, A/Wyoming/3/2003 (X-147), A/Wellington/1/2004-like strain, A/Wellington/1/2004 (IVR-139), A/California/7/2004-like strain, A/New York/55/200 (NYMC X-157), A/Wisconsin/67/2005-like strain, A/Wisconsin/67/2005 (NYMC X-161-B), A/Brisbane/10/2007-like virus, A/Brisbane/10/2007 (IVR-147), A/Uruguay/716/2007 NYMC X-175C, A/Beijing/353/89-like, A/Guizhou/54/89, A/Beijing/353/89, A/Beijing/32/92, A/Shangdong/9/93, A/Johannesburg/33/94, A/Wuhan/359/95-like, A/Nanchang/933/95 (RESVIR-9), A/Sydney/5/97-like, A/Sydney/5/97 (IVR-108), A/Moscow/10/99-like, A/Panama/2007/99 (RESVIR-17), A/Fujian/411/2002-like, A/Wyoming/3/2003 (X-147), A/California/7/2004-like, A/New York/55/2004 NYMC (X-157, A/Wisconsin/67/2005 (NYMC X-161), A/Wisconsin/67/2005-like, A/Wisconsin/67/2005 (NYMC X-161-B), A/Brisbane/10/2007-like virus, A/Uruguay/716/2007 NYMC X-175C.

B Strains

B/Beijing/184/93-like strain, B/Yamanashi/166/98, B/Sichuan/379/99-like strain

B/Johannesburg/5/99, B/Sichuan/379/99-like strain, B/Johannesburg/5/99

B/Hong Kong/330/2001-like s., B/Shangdong/7/97, B/Hong Kong/330/2001-like s., B/Brisbane/32/2002, B/Shanghai/361/2002-like strain, B/Jiangsu/10/2003, B/Malaysia/2506/2004-like strain, B/Malaysia/2506/2004, B/Florida/4/2006-like virus B/Brisbane/3/2007, B/Yamagata/16/88, B/Panama/45/90, B/Harbin/7/94, B/Beijing/184/93-like, B/Beijing/184/93-like, B/Yamanashi/166/98, B/Sichuan/379/99-like, B/Johannesburg/5/99, B/Hong Kong/330/2001-like, B/Shangdong/7/97, B/Shanghai/361/2002-like, B/Jiangsu/10/2003, B/Malaysia/2506/2004-like, B/Malaysia/2506/2004, B/Florida/4/2006-like virus, B/Brisbane/3/2007, B/Brisbane/60/2008-like virus, B/Brisbane/60/2008

Suitably the influenza virus strain or strains from which the whole, subunit or split influenza virus preparations are derived are interpandemic (seasonal) strain(s), or strain(s) being associated with a pandemic outbreak or having the potential to be associated with a pandemic outbreak.

Interpandemic strains are for example strains which circulate globally during interpandemic periods such as but not limited to: H1N1, H1N2, H3N2 or B. Commercially available influenza vaccines are a trivalent combination including one influenza B strain and two influenza A strains (H1N1, H3N2).

The features of an influenza virus strain that give it the potential to cause a pandemic or an outbreak of influenza disease associated with pandemic influenza strains are: it contains a new haemagglutinin compared to the haemagglutinin in the currently circulating strains and therefore nearly all people are immunologically naive; it is capable of being transmitted horizontally in the human population; and it is pathogenic for humans. A new haemagglutinin may be one which has not been evident in the human population for an extended period of time, probably a number of decades, such as H2. Or it may be a haemagglutinin that has not been circulating globally in the human population before, for example H5, H9, H7 or H6 which are found in avian species (birds). In either case the majority, or at least a large proportion of, or even the entire population has not previously encountered the antigen and/or is immunologically naïve to it. At present, the influenza A virus that has been identified by the WHO as one that potentially could cause a pandemic in humans is the highly pathogenic H5N1 avian influenza virus. Therefore, the pandemic vaccine disclosed herein suitably comprises H5N1, H9N2 or H7N1.

The influenza virus strain may be a pandemic strain. Suitable pandemic strains are, but not limited to: H5N1, H5N8, H5N9, H7N4, H9N2, H7N7, H7N3, H2N2 and H7N1. Other pandemic strains in human: H7N3, H10N7, H5N2 and H7N2. An influenza strain which is a pandemic strain or a strain susceptible to be associated with a pandemic will be referred to in short in this document as a "pandemic strain".

The whole, subunit or split influenza virus preparations as described herein may be egg-derived or cell-culture derived. For example, whole, subunit or split influenza virus preparations according to the invention may be derived from the conventional embryonated egg method, by growing influenza virus in eggs and purifying the harvested allantoic fluid. Eggs can be accumulated in large numbers at short notice. Alternatively, they may be derived from any of the new generation methods using cell or cell culture to grow the virus or express recombinant influenza virus surface antigens. Suitable cell substrates for growing the virus include for example dog kidney cells such as MDCK or cells from a clone of MDCK, MDCK-like cells, monkey kidney cells such as AGMK cells including Vero cells, suitable pig cell lines, or any other mammalian cell type suitable for the production of influenza virus for vaccine purposes. Suitable cell substrates also include human cells e.g. MRC-5 cells or the Per.C6 cell line.

In a particular embodiment, whole, subunit or split influenza virus preparations of the invention are derived from primary cells such as chicken embryo fibroblasts and avian cell lines such as chicken or duck cell lines (e.g. EBx cell line such as EB14 derived from chicken or EB24 or EB66 derived from duck embryonic stem cells, disclosed in WO03/076601 (US2004058441A1) and in WO08/129,058 (US2010062489A1) are also included. Suitable insect cells are Sf9 or Hi5. In a particular embodiment the whole, subunit or split influenza virus preparations of the invention are derived from EB66 cells.

In one aspect the invention relates to a split influenza virus preparation or subunit influenza preparation obtained or obtainable in the process of the present invention.

In one aspect the invention relates to a process for preparing a pharmaceutical composition, comprising the steps of: (i) providing a split influenza virus preparation or subunit influenza preparation by any of the processes disclosed herein, and (ii) admixing said split influenza virus preparation or subunit influenza preparation with a pharmaceutically acceptable carrier to prepare the vaccine.

In one aspect the invention relates to a pharmaceutical and/or immunogenic composition obtained or obtainable by any the processes of the invention.

A pharmaceutical composition of the invention containing a split influenza virus preparation or subunit influenza preparation may be referred to as an immunogenic composition or a vaccine herein.

Medical Treatment

In one aspect the invention relates to a method of inducing an immune response into a human subject, said method comprising administering to the subject the pharmaceutical and/or immunogenic composition or vaccine of the invention as described herein.

In a further embodiment of the invention there is provided a pharmaceutical/immunogenic composition or vaccine as described herein for use in medicine.

In a further embodiment of the invention there is provided a pharmaceutical/immunogenic composition or vaccine as described herein for use in the treatment and/or prevention of disease caused by the influenza virus in a subject.

In a further embodiment of the invention there is provided the use of a pharmaceutical/immunogenic composition or vaccine as described herein in the manufacture of a medicament for the treatment and/or prevention of disease caused by influenza virus in a subject.

In a particular embodiment of the invention, the subject administered with a pharmaceutical/immunogenic composition or vaccine as described herein is immune-compromised. In a particular embodiment, the subject is over 60 years old, in particular 65 or more years old. In a further embodiment, the subject is an infant/child, in particular than 6 months old, and even more particular in particular between 6 and 23 months of age.

Adjuvant

In one aspect a pharmaceutical or immunogenic composition of the invention is not adjuvanted. In another aspect a pharmaceutical or immunogenic composition of the invention comprises an adjuvant, for example an oil in water emulsion.

In one aspect an adjuvant according to the present invention is an emulsion, in particular, an oil-in-water emulsion, and may optionally comprise other immunostimulants.

In a specific embodiment, an oil-in-water emulsion comprises a metabolisable, non-toxic oil, such as squalane or squalene, optionally a tocol such as tocopherol in particular alpha tocopherol (and optionally both squalene and alpha tocopherol) and an emulsifier (or surfactant) such as the non-ionic surfactant polyoxyethylene sorbitan monooleate (TWEEN-80™ or POLYSORBATE 80™). Mixtures of surfactants can be used polyoxyethylene sorbitan monooleate (TWEEN-80™ or POLYSORBATE 80™)/sorbitan trioleate (SPAN 85™) mixtures, or polyoxyethylene sorbitan monooleate (TWEEN-80™ or POLYSORBATE 80™)/t-octylphenoxypolyethoxyethanol (TRITON X-100™) mixtures.

Tocols (e.g. vitamin E) are also used in oil emulsions adjuvants (EP0382271B1; U.S. Pat. No. 5,667,784; WO95/17210). Tocols used in oil emulsions (optionally oil-in-water emulsions) may be formulated as described in U.S. Pat. No. 5,650,155A; U.S. Pat. No. 5,667,784A; EP0382271B1, in that the tocols may be dispersions of tocol droplets, optionally comprising an emulsifier, of optionally less than 1 micron in diameter. Alternatively, the tocols may be used in combination with another oil, to form the oil phase of an oil emulsion. Examples of oil emulsions which may be used in combination with the tocol are described herein, such as the metabolisable oils described above.

In an oil-in-water emulsion, the oil and emulsifier should be in an aqueous carrier. The aqueous carrier may be, for example, phosphate buffered saline or a citrate buffer.

In one aspect, the oil in water emulsion has one of the following compositions:

from 0.5 to 11 mg squalene, from 0.05 to 5% polyoxyethylene sorbitan monooleate (TWEEN-80™ or POLYSORBATE 80™) and optionally, from 2 to 12% alpha-tocopherol; or about 5% squalene, about 0.5% polyoxyethylene sorbitan monooleate (TWEEN-80™ or POLYSORBATE 80™) and about 0.5% sorbitan trioleate (SPAN 85™). This adjuvant is called MF59.

Pharmaceutical and/or Immunogenic Compositions

In one embodiment pharmaceutical and/or immunogenic compositions of the invention comprise hemagglutinin of one or more strains at an amount of about 15 μg/strain, about 7.5 μg/strain, about 3.8 μg/strain, about 1.9 μg/strain or 5 μg/strain.

Some currently existing vaccines have residual detergent present as a result of the use of that detergent in the splitting process. In other cases there may be addition of the detergent to the vaccine antigen. In the present invention the use of a detergent, such as a non-ionic surfactant, such as t-octylphenoxypolyethoxyethanol (TRITON X-100™), added after splitting of the virus (and suitably prior to filtration and suitably before inactivation), provides a ratio of between 1.5 and 15 t-octylphenoxypolyethoxyethanol (TRITON X-100™): HA in the final monovalent bulk produced after the manufacturing process, assessed by the weight/volume ratios of the t-octylphenoxypolyethoxyethanol (TRITON X-100™) and HA, suitably between 2.5 and 15, suitably between 3 and 15, suitably between 3.3 and 15, or a higher ratio.

In one aspect the invention relates to a pharmaceutical or immunogenic composition comprising an influenza virus hemagglutinin (HA) and a non ionic surfactant wherein the weight/volume ratio of non-ionic surfactant to hemagglutinin is between 1 and 15. The surfactant may be t-octylphenoxypolyethoxyethanol (TRITON X-100™). The HA concentration may be between 2 and 200 μg per strain per ml. The t-octylphenoxypolyethoxyethanol (TRITON X-100™) concentration may be between 10 and 500 μg/ml.

In one aspect the invention relates to a vaccine made from multiple influenza strains, wherein at least one component is manufactured according the process of the invention. Suitably a vaccine comprising 2 or 3 strains are made using a process of the invention.

In one aspect pharmaceutical or immunogenic composition of the invention comprising multivalent strains, have a ratio of between 1 and 15 t-octylphenoxypolyethoxyethanol (TRITON X-100™): HA in the final vaccine, assessed by the weight/volume ratios of the t-octylphenoxypolyethoxyethanol (TRITON X-100™) and HA, suitably, such as between 1.5 and 15, such as between 2 and 15, such as between 2.5 and 15, suitably between 3 and 15, suitably between 3.3 and 15, or a higher ratio.

Split Influenza Preparation

The preparation process for a split influenza virus preparation for use in pharmaceutical or immunogenic compositions may include a number of different filtration and/or other separation steps such as ultracentrifugation, ultrafiltration, zonal centrifugation and chromatography (e.g. ion exchange) steps in a variety of combinations, and optionally an inactivation step e.g. with heat, formaldehyde or β-propiolactone or U.V. which may be carried out before or after splitting. The splitting process may be carried out as a batch, continuous or semi-continuous process. A preferred splitting and purification process for a split immunogenic composition is described in WO 02/097072 (U.S. Pat. No. 7,316,813B2) which is incorporated by reference in its entirety.

Such a process suitably comprises the steps of:

Initial filtration, virus splitting, filtration, inactivation, filtration; wherein the filtration may be an ultrafiltration step.

Accordingly, in one embodiment there is provided processes of the invention further comprising the step of inactivating the split influenza virus preparation. Inactivation can be performed by any method known to the skilled person including, but is not limited to using formaldehyde. Inactivation may be performed at any stage of the process following step (ii). In a particular embodiment of the invention inactivation is performed after step (iii).

The process of the invention comprise at least one filtration step (step iv), but may comprise 1, 2, 3, 4, 5, 6, 7, 8, 9 or more filtration steps in addition to that of step (iv). For example, the split influenza virus preparation may be filtered using a series of filter of differing size e.g. 0.5 µm, 0.45 µm and/or 0.2/0.22 µm filters. In a particular embodiment the filtering step (step iv) is performed using one or more filter membranes, wherein at least one filter membrane is sterile grade (e.g. 0.2 µm or 0.22 µm). In a further embodiment there is provided processes of the invention comprising the step of filtering the split influenza virus preparation in addition to the filtration step of step (iv). In a particular embodiment, the filtering step in addition to that of step iv) is performed using a sterile grade filter (for example a 0.2 µm or 0.22 µm filter).

In a further embodiment, there are provided processes of the invention further comprising the step of ultracentrifuging the split influenza virus preparation. Suitably, ultrafiltration is performed using a cellulose acetate membrane with about 20 kDa MW cut-off In a further embodiment, there are provided processes of the invention further comprising the step of clarifying the whole virus preparation.

In a further embodiment, there are provided processes of the invention comprising the step of ultracentrifuging the whole virus preparation.

Preferred split influenza virus preparations according to the invention comprise a residual amount of polyoxyethylene sorbitan monooleate (TWEEN-80™ or POLYSORBATE 80™) and/or t-octylphenoxypolyethoxyethanol (TRITON X-100™) remaining from the production process, although these may be added or their concentrations adjusted after preparation of the split antigen. In one embodiment both polyoxyethylene sorbitan monooleate (TWEEN-80™ or POLYSORBATE 80™) and t-octylphenoxypolyethoxyethanol (TRITON X-100™) are present. The preferred ranges for the final concentrations of polyoxyethylene sorbitan monooleate (TWEEN-80™ or POLYSORBATE 80™) in the vaccine dose, arising from the antigenic preparation, are:

polyoxyethylene sorbitan monooleate (TWEEN-80™ or POLYSORBATE 80™): 0.01 to 1%, or about 0.1% (v/v)

In a specific embodiment, the final concentration for polyoxyethylene sorbitan monooleate (TWEEN-80™ or POLYSORBATE 80™) arising from the split influenza virus preparation, ranges from 0.025%-0.09% w/v. In another specific embodiment, the split influenza virus preparation is provided as a 2 fold concentrated mixture, which has a polyoxyethylene sorbitan monooleate (TWEEN-80™ or POLYSORBATE 80™) concentration ranging from 0.025%-0.2% (w/v) and has to be diluted two times upon final formulation with the adjuvanted (or the buffer in the control formulation).

In one embodiment, the split influenza virus preparation is prepared in the presence of low level of thiomersal, or in the absence of thiomersal. In another embodiment, the resulting split influenza virus preparation is stable in the absence of organomercurial preservatives, in particular the preparation contains no residual thiomersal. In particular the split influenza virus preparation comprises a haemagglutinin antigen stabilised in the absence of thiomersal, or at low levels of thiomersal (generally 5 µg/ml or less). Specifically the stabilization of B influenza strain is performed by a derivative of alpha tocopherol, such as alpha tocopherol succinate (also known as vitamin E succinate, i.e. VES).

Such preparations and methods to prepare them are disclosed in WO 02/097072 (U.S. Pat. No. 7,316,813B2) which is incorporated by reference in its entirety.

A preferred composition contains three inactivated split influenza virus preparation prepared from the WHO recommended strains of the appropriate influenza season.

In one embodiment, the split influenza virus preparation or subunit influenza preparation and the adjuvant according to the invention are contained in the same container. It is referred to as 'one vial approach'. In another embodiment, the vial is a pre-filled syringe. In an alternative embodiment, the split influenza virus preparation or subunit influenza preparation and adjuvant according to the invention are contained in separate containers or vials and admixed shortly before or upon administration into the subject. It is referred to as 'two vials approach'. Suitably the two vials approach consists of 0.5 ml of concentrated split influenza virus preparation or subunit influenza preparations as described herein presented in a type I glass vial (antigen container) and of a pre-filled type I glass syringe containing 0.5 ml of the adjuvant (adjuvant container). Alternatively the two vial approach is presented in 2 vials (one for the antigen one for the adjuvant, of 10 doses each) for mixture prior to the administration to the first patient within 24 hours at room temperature and subsequent storage at 4° C. for a short period of time (e.g. up to one week) for subsequent administration. At the time of injection, the content of the multidose vial or the syringe containing the adjuvant is injected into the vial that contains the concentrated split influenza virus preparation or subunit influenza preparation. After mixing the content is withdrawn into the syringe and the needle is replaced by an intramuscular needle. One dose of the adjuvanted split influenza virus preparation or subunit influenza preparation (pharmaceutical or immunogenic composition) corresponds to 0.5 ml.

In one embodiment, each human dose of the pharmaceutical or immunogenic composition contains a 15 µg of HA per influenza strain per dose, as determined by SRID. This is particularly useful for the elderly population.

An important aspect of the present invention is the fact that the influenza antigen(s) can be used at lower amounts than had previously been thought useful, suitably at a level of less than 15 µg HA per strain of virus, for example between 1 and 10 µg HA per strain, per human dose of the immunogenic composition.

Accordingly, in one embodiment, each human dose of the pharmaceutical or immunogenic composition contains a low dose of haemagglutinin (HA), defined as an amount of less than 15 µg of HA per dose, suitably less than 10 µg, as measured by single radial immunodiffusion (SRD) (J. M. Wood et al.: J. Biol. Stand. 5 (1977) 237-247; J. M. Wood et al., J. Biol. Stand. 9 (1981) 317-330). In a specific embodiment, the human dose of the immunogenic composition comprises a dose of haemagglutinin (HA) per strain at a level of about 10 µg, for example between 5 and 15 µg, suitably between 6 and 14 µg, for example between 7 and 13 µg or between 8 and 12 µg or between 9 and 11 µg, or 10 µg. In a further embodiment, the human dose of the immunogenic composition comprises a dose of haemagglutinin (HA) per strain at a level of about 5 µg, for example between 1 and 9 µg, or between 2 and 8 µg or suitably between 3 and 7 µg or 4 and 6 µg, or 5 µg. Suitable amounts are 1.9 µg, 2.5 µg, 3.8 µg, 5.0 µg, 7.5 µg, or 10 µg HA or any suitable amount of HA lower than 15 µg which would have be determined such that the vaccine composition meets the efficacy criteria as defined herein. Advantageously an HA dose of 1 µg of HA or even less such as 0.5 µg of HA that would allow meeting the regulatory criteria defined in Tables C or/and D may be used. A suitable amount of HA is for example any of 1, 2, 3, 4, 5, 6, 7, 8, 9, 10, 11, 12, 13, 14, μg (w/v) per influenza strain per human dose of the immunogenic composition. Said low amount of HA may be as low as practically feasible provided that it allows to formulate a vaccine which meets the international e.g. EU or FDA criteria for efficacy, as detailed below (see Table 3 and 4 and the specific parameters as set forth).

A pharmaceutical or immunogenic composition dose of 0.5 ml is suitably used. A pharmaceutical or immunogenic composition dose of 1 ml (0.5 ml adjuvant plus 0.5 ml antigen preparation) is also suitable. Advantageously, a pharmaceutical or immunogenic composition dose according to the invention, in particular a low HA amount vaccine, may be provided in a smaller volume than the conventional injected split flu vaccines, which are generally about 0.5, 0.7 or 1 ml per dose. The low volume doses according to the invention are suitably below 500 μl, typically below 300 μl and suitably not more than about 200 μl or less per dose. Slight adaptation of the dose volume will be made routinely depending on the HA concentration in the original bulk sample, or depending on the delivery route with smaller doses being given by the intranasal or intradermal route, or depending on the target population (for example infants may receive half of an adult human dose).

The influenza pharmaceutical or immunogenic compositions of the invention suitably meet certain international criteria for vaccines. Standards are applied internationally to measure the efficacy of influenza vaccines. Serological variables are assessed according to criteria of the European Agency for the Evaluation of Medicinal Products for human use (CHMP/BWP/214/96, Committee for Proprietary Medicinal Products (CPMP). *Note for harmonization of requirements for influenza vaccines*, 1997. CHMP/BWP/214/96 circular No 96-0666:1-22) for clinical trials related to annual licensing procedures of influenza vaccines (Table 3 or Table 4). The requirements are different for adult populations (18-60 years) and elderly populations (>60 years) (Table C). For interpandemic influenza vaccines, at least one of the assessments (seroconversion factor, seroconversion rate, seroprotection rate) should meet the European requirements, for all strains of influenza included in the vaccine. The proportion of titres equal or greater than 1:40 is regarded most relevant because these titres are expected to be the best correlate of protection [Beyer W et al. 1998. Clin Drug Invest.; 15:1-12].

As specified in the "Guideline on dossier structure and content for pandemic influenza vaccine marketing authorisation application. (CHMP/VEG/4717/03, Apr. 5, 2004, or more recently EMEA/CHMP/VWP/263499/2006 of 24 Jan. 2007 entitled 'Guidelines on flu vaccines prepared from viruses with a potential to cause a pandemic', available on www.emea.eu.int), in the absence of specific criteria for influenza vaccines derived from non circulating strains, it is anticipated that a pandemic candidate vaccine should (at least) be able to elicit sufficient immunological responses to meet suitably all three of the current standards set for existing vaccines in unprimed adults or elderly subjects, after two doses of vaccine. The EMEA Guideline describes the situation that in case of a pandemic the population will be immunologically naive and therefore it is assumed that all three CHMP criteria for seasonal vaccines will be fulfilled by pandemic candidate vaccines. No explicit requirement to prove it in pre-vaccination seronegative subjects is required.

The compositions of the present invention suitably meet at least one such criteria for the strain included in the composition (one criteria is enough to obtain approval), suitably at least two, or typically at least all three criteria for protection as set forth in Table 3.

TABLE 3

(CHMP criteria)

|  | 18-60 years | >60 years |
|---|---|---|
| Seroconversion rate* | >40% | >30% |
| Conversion factor** | >2.5 | >2.0 |
| Protection rate*** | >70% | >60% |

*Seroconversion rate is defined as the proportion of subjects in each group having a protective post-vaccination titre ≥ 1:40. The seroconversion rate simply put is the % of subjects who have an HI titre before vaccination of <1:10 and ≥1:40 after vaccination. However, if the initial titre is ≥1:10 then there needs to be at least a fourfold increase in the amount of antibody after vaccination.
**Conversion factor is defined as the fold increase in serum HI geometric mean titres (GMTs) after vaccination, for each vaccine strain.
***Protection rate is defined as the proportion of subjects who were either seronegative prior to vaccination and have a (protective) post-vaccination HI titre of ≥ 1:40 or who were seropositive prior to vaccination and have a significant 4-fold increase in titre post-vaccination; it is normally accepted as indicating protection.

FDA uses slightly different age cut-off points, but their criteria are based on the CHMP criteria. Appropriate endpoints similarly include: 1) the percent of subjects achieving an HI antibody titer ≥1:40, and 2) rates of seroconversion, defined as a four-fold rise in HI antibody titer post-vaccination. The geometric mean titer (GMT) should be included in the results, but the data should include not only the point estimate, but also the lower bound of the 95% confidence interval of the incidence rate of seroconversion, and the day 42 incidence rate of HI titers ≥1:40 must exceed the target value. These data and the 95% confidence intervals (CI) of the point estimates of these evaluations should therefore be provided. FDA draft guidance requires that both targets be met. This is summarised in Table 4.

TABLE 4

|  | 18-64 years | >64 years |
|---|---|---|
| Seroconversion rate * | >40% | >30% |
| Rate of HI titers ≥ 1:40 | >70% | >60% |

* The seroconversion rate is defined as: a) for subjects with a baseline titer ≥ 1:10, a 4-fold or greater rise; or b) for subjects with a baseline titer < 1:10, a rise to ≥ 1:40. These criteria must be met at the lower bound of the 95% CI for the true value.

In an alternative embodiment, the compositions of the present invention suitably meet at least one such criteria for the strain included in the composition, suitably both criteria for protection as set forth in Table 4.

Suitably this effect is achieved with a low dose of antigen, such as with 7.5 μg HA or even a lower antigen dose such as 3.8 μg or 1.9 μg of HA.

Suitably any or all of such criteria are also met for other populations, such as in children and in any immuno-compromised population.

In one aspect of the invention, the human dose of the pharmaceutical or immunogenic composition contains an haemagglutinin (HA) from a single influenza strain, and is referred to as a "monovalent" influenza composition. In another aspect of the invention, the human dose of the pharmaceutical or immunogenic composition comprises haemagglutinin (HA) from more than one influenza strain, and is referred to as a "multivalent" influenza composition. A suitable multivalent composition according to the invention is a bivalent composition (comprising haemagglutinin (HA) from two influenza virus strains such as but not exclusively two strains associated to a pandemics or susceptible to be associated with a pandemic, e.g. H5=H2), a trivalent composition (comprising haemagglutinin (HA)

from three influenza virus strains, optionally from two A strains, and one B strain such as but not limited to B/yamagata or B/Victoria), a quadrivalent composition (comprising haemagglutinin (HA) from four influenza virus strains) or a pentavalent composition (comprising haemagglutinin (HA) from five influenza virus strains). A suitable quadrivalent composition comprises haemagglutinin from two A strains and two B strains from different lineage (such as B/yamagata or B/Victoria). Such a composition comprising a second B strain is particularly suitable for very young children especially where prior exposure or priming is important. Alternatively a quadrivalent composition comprises haemagglutinin from three A strains (optionally H1N1, H3N2, and one A strain associated to a pandemic or susceptible to be associated to a pandemic) and one B strain (such as B/yamagata or B/Victoria). Another alternative quadrivalent composition comprises haemagglutinin from four A strains from a strain associated to a pandemic or susceptible to be associated to a pandemic, such as avian strains such as H5+H2+H7+H9. Specifically a multivalent adjuvanted pandemic composition such as a pandemic bi-valent (e.g. H5+H2) or trivalent or quadrivalent (e.g. H5+H2+H7+H9) offers the advantage of a pre-emptive immunisation against pandemic influenza A threats subtypes and durable priming against threat subtypes. Typically two doses are given from 6 weeks of age using a convenient schedule (e.g., 6-12 months apart), and optionally a periodic booster foreseen (e.g., 10 yrs). Optionally, such a pandemic vaccine may be combined with a seasonal vaccine.

A multivalent composition can also comprise more than 5 influenza strains such as 6, 7, 8, 9 or 10 influenza strains.

When two B strains are used in a multivalent seasonal composition, they can be from two different lineages (optionally from B/Victoria and B/Yamagata). At least one of said B strain, suitably both B strains, will be from a circulating lineage. Such a composition is particularly suitable for children. Suitably when the multivalent composition for use in children includes two B strains the quantity of antigen normally allotted to the B strain is divided among the two B strains. Specifically, the adjuvanted quadrivalent (H1+H3+both B lineages) influenza vaccine offers the advantage of enhanced prophylaxis for naïve children as its superior efficacy compared to unadjuvanted vaccines (in terms of both homologous and drift protection, and its efficacy against two circulating B lineages) and of possible year-round immunization based on age. One dose or two doses are suitably administered as early as from the age of 6 weeks, or between 6 to 35 months.

In a specific embodiment, the human dose of the pharmaceutical or immunogenic composition is a trivalent immunogenic or vaccine composition comprising haemagglutinin (HA) from two A strains (optionally H1N1, H3N2) and one B strain. Suitably the HA per strain is a low amount of HA (optionally 10 µg HA per strain or below) and is as defined above. Suitably the HA per strain is at about or below 5 µg, at about 2.5 µg or below. An adjuvant as defined herein may be included and in particular as defined in Table 1. Suitably the adjuvant composition is an oil-in-water emulsion comprising squalene, alpha-tocopherol, and polyoxyethylene sorbitan monooleate (TWEEN-80™ or POLYSORBATE 80™) at an amount of between 5-6 mg, between 5-6 mg and between 2-3 mg per dose, respectively. Alternatively, the adjuvant composition is an oil-in-water emulsion comprising squalene, alpha-tocopherol, and polyoxyethylene sorbitan monooleate (TWEEN-80™ or POLYSORBATE 80™) at an amount of between 2.5-3.5 mg, between 2-3 mg and between 1-2 mg per dose, respectively. These adjuvanted immunogenic compositions or vaccines are particularly suitable for the adult (18-60 years) or older children (3-17 years) population, and may provide cross-protection against H3N2 drift variants and against B strain from a different lineage.

In another specific embodiment, the human dose of the immunogenic composition is a quadrivalent immunogenic or vaccine composition comprising haemagglutinin (HA) from two A strains (optionally H1N1, H3N2) and two B strains (optionally from a different lineage, such as from B/Victoria and B/Yamagata). In another specific embodiment, the human dose of the immunogenic composition is a quadrivalent immunogenic or vaccine composition comprising haemagglutinin (HA) from two interpandemic A strains (optionally H1N1, H3N2), one B strain and one A strain associated to a pandemic or susceptible to be associated with a pandemic (optionally H5N1, H9N2, H7N7, H5N8, H5N9, H7N4, H7N3, H2N2, H10N7, H5N2, H7N2 and H7N1). In another specific embodiment, the human dose of the immunogenic composition is a quadrivalent immunogenic or vaccine composition comprising haemagglutinin (HA) from three interpandemic A strains (optionally H1N1, and two H3N2 strains) and one B strain. Suitably the HA per strain per dose is at about 15 µg. Suitably the HA per strain is a low amount of HA (optionally at about 10 µg HA per strain per dose or below, so as to achieve a maximum of 40-45 µg HA per dose of quadrivalent composition) and is as defined above. Suitably the HA per strain is at about or below 5 µg, at about 2.5 µg or below. An adjuvant where present may be any adjuvant as described herein.

In another specific embodiment, the human dose of the pharmaceutical or immunogenic composition is a pentavalent immunogenic or vaccine composition comprising haemagglutinin (HA) from two interpandemic A strains (optionally H1N1, H3N2), two B strains (optionally from a different lineage, such as from B/Victoria and B/Yamagata) and one A strain associated to a pandemic or susceptible to be associated with a pandemic (optionally H5N1, H9N2, H5N8, H5N9, H7N4, H7N7, H7N3, H2N2, H10N7, H5N2 and H7N1). In another specific embodiment, the human dose of the pharmaceutical or immunogenic composition is a pentavalent immunogenic or vaccine composition comprising haemagglutinin (HA) from three interpandemic A strains (optionally H1N1, and two H3N2 strains) and two B strains (optionally from a different lineage, such as from B/Victoria and B/Yamagata). Suitably the HA per strain is a low amount of HA (optionally 10 µg HA per strain or below) and is as defined above.

In one embodiment the multivalent compositions are adjuvanted, suitably with a squalene-based oil-in-water emulsion adjuvant. Accordingly in a specific embodiment the invention provides an influenza immunogenic composition comprising squalene and HA wherein the weight ratio squalene:total amount of HA (all influenza strains included) is in the range of between about 50-150 or about 150-400 (e.g. about 200-300). Such compositions are suitably but not exclusively for use in the elderly population and best balances reactogenicity and immunogenicity. In another embodiment, the invention provides an influenza immunogenic composition comprising squalene and HA wherein the weight ratio squalene:total amount of HA (all influenza strains included) is between about 50-400, e.g. about 50-100, 75-150, 75-200, 75-400, 100-200, 100-250 or 200-400. The ratio will suitably be such that at least two, suitably all three criteria (Table C or D) for protection will be met for a specific population. Suitably the HA is from at least three, at least four influenza strains. Suitably three seasonale (e.g.

H1N1, H3N2, B) strains are present. Suitably when four strains are present they are from the group of: four seasonal strains (e.g. H1N1, H3N2, two B strains; or H1N1, B, two H3N2 strains) or the group of one pandemic (e.g. avian) strain plus three seasonal strains (e.g. H1N1, H3N2, B).

General Language

The teaching of all references in the present application, including patent applications and granted patents, are herein fully incorporated by reference. Any patent application to which this application claims priority is incorporated by reference herein in its entirety in the manner described herein for publications and references.

For the avoidance of doubt the terms 'comprising', 'comprise' and 'comprises' herein is intended by the inventors to be optionally substitutable with the terms 'consisting of', 'consist of', and 'consists of', respectively, in every instance. Embodiments herein relating to "vaccine compositions" of the invention are also applicable to embodiments relating to "immunogenic compositions" of the invention, and vice versa. The term "about" (or "around") in all numerical values allows for a 5% variation, i.e. a value of about 1.25% would mean from between 1.19%-1.31%.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the measurement, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The invention will be further described by reference to the following, non-limiting, examples:

EXAMPLES

Example 1

An exemplary production process for the influenza virus strains based on the process described in WO02/097072 (U.S. Pat. No. 7,316,813B2) and the steps summarized in FIG. 1 was compared to two other processes as outlined in FIG. 1.

The pandemic H1N1v strain (A/California/7/2009 X-179A) was produced according to Process A performed in the presence or the absence of t-octylphenoxypolyethoxyethanol (TRITON X-100™) (FIG. 1). When applying the manufacturing process A it was observed that approximately 50% of haemagglutinin (HA) as measured by HPLC was lost at the two 0.2 jam filtration steps (FIG. 2).

Three test lots of A/California/7/2009 X-179A H1N1v monovalent bulks were produced using the manufacturing process A amended by the addition of t-octylphenoxypolyethoxyethanol (TRITON X-100™) in the dilution buffer added after the splitting gradient, just before inactivation with formaldehyde (described herein as "process A+t-octylphenoxypolyethoxyethanol (TRITON X-100™)").

Process steps upstream of the addition of t-octylphenoxypolyethoxyethanol (TRITON X-100™) were unchanged.

As shown in Table 5, the addition of t-octylphenoxypolyethoxyethanol (TRITON X-100™) after splitting and before filtration produced an improved yield of HA in comparison to the process without t-octylphenoxypolyethoxyethanol (TRITON X-100™) at this stage.

The particle sizes prior to filtration were found to be reduced compared those seen with process A which does not comprise the addition of t-octylphenoxypolyethoxyethanol (TRITON X-100™).

The HA yield at the monovalent bulk step is of 39 μg/egg as compared to 15 μg/egg in process A+t-octylphenoxypolyethoxyethanol (TRITON X-100™), which corresponds to a 2.6-fold increase.

The ratio of t-octylphenoxypolyethoxyethanol (TRITON X-100™) content/HA content in H1N1v final bulk is higher when using process A+t-octylphenoxypolyethoxyethanol (TRITON X-100™), as compared to the process A alone without t-octylphenoxypolyethoxyethanol (TRITON X-100™).

The modified purification process (process A+t-octylphenoxypolyethoxyethanol (TRITON X-100™)) was also carried out on an H3N2 strain with the addition of t-octylphenoxypolyethoxyethanol (TRITON X-100™) at the same point in the process as used for the H1N1v strain. The addition of t-octylphenoxypolyethoxyethanol (TRITON X100™) in a dilution buffer after the splitting gradient, just before inactivation with formaldehyde, resulted in a 2-3 fold increase in the A/H2N2/Nanchang/933/95 RESVIR-9 strain.

TABLE 5

|  | | A/H1N1v strain | H3N2 strain |
|---|---|---|---|
|  | Process A | Process A with t-octylphenoxypolyethoxyethanol (TRITON X-100 ™) buffer | Fluarix process with t-octylphenoxypolyethoxyethanol (TRITON X-100 ™) |
| HA yield per egg | 15 μg/egg ⇒ | 39 μg/egg | 63 μg/egg |
| HA content monovalent bulks | 20-50 μg/ml | 140-190 μg/ml | 80-280 μg/ml |
| HA content final bulks | 15 μg/ml | 15 μg/ml | 90 μg/ml |
| t-octylphenoxypolyethoxyethanol (TRITON X-100 ™) content monovalent bulks | 0 μg/ml | 470-600 μg/ml | 190-440 μg/ml |
| t-octylphenoxypolyethoxyethanol (TRITON X-100 ™) content final bulks | 13-17 μg/ml | 60-103 μg/ml | 80-105 μg/ml |
| t-octylphenoxypolyethoxyethanol (TRITON X-100 ™) Specification in final bulk | 11-20 μg/ml | 50-170 μg/ml | 50-170 μg/ml |

TABLE 5-continued

| | A/H1N1v strain | | H3N2 strain |
|---|---|---|---|
| | Process A | Process A with t-octylphenoxypolyethoxyethanol (TRITON X-100 ™) buffer | Fluarix process with t-octylphenoxypolyethoxyethanol (TRITON X-100 ™) |
| Ratio t-octylphenoxypolyethoxyethanol (TRITON X-100 ™)/HA | 0.7-1.3 | 3.3-11.3 | 0.6-1.9 |

Example 2

Impact on the Quality of the Antigen

The potential impact of t-octylphenoxypolyethoxyethanol (TRITON X-100™) on the quality of the product was evaluated by particle size measurements, as well as purity and protein pattern analysis by SDS-PAGE.

Profile analysis by Gel and Western blot.

The addition of t-octylphenoxypolyethoxyethanol (TRITON X-100™) in the process is shown to improve purity, as the ratio of total protein/HA content is shown to be reduced from 2.5 to 1.7.

As seen in FIG. 3, the pattern of peptide bands in SDS-PAGE gels is unchanged whether t-octylphenoxypolyethoxyethanol (TRITON X-100™) was used or not in the manufacturing process. An increased portion of HA (approximately 3-fold seen by densitometry) is observed in lots produced with t-octylphenoxypolyethoxyethanol (TRITON X-100™). This finding is consistent with the improved protein/HA ratio.

Example 3

Preliminary Quality Data on the 1St Pandemic Monovalent Bulks Lots Manufactured with t-octylphenoxypolyethoxyethanol (TRITON X100™)

Preliminary quality data obtained on three monovalent bulks produced using the t-octylphenoxypolyethoxyethanol (TRITON X-100™) process are presented in Table 6.

The data obtained are in line with what was seen on test lots produced for the 1$^{st}$ evaluations of the process: higher HA yields and higher purity profile.

Batch Analysis Data on H1N1v Monobulks Manufactured with the t-octylphenoxypolyethoxyethanol (TRITON X-100™) Process

| | A/California/7/2009 NYMC X-179A Lot N° | | |
|---|---|---|---|
| Parameter | DFLSIDA030 (AFLSFDA107) | DFLSIDA031 (AFLSFDA109) | DFLSIDA032 (AFLSFDA111) |
| HA content SRD (µg/ml) | ~180 | >=200 | >=200 |
| Protein (µg/mL) | 259 | 297 | 325 |
| Tween (µg/mL) | 503 | ND | ND |
| t-octylphenoxypolyethoxyethanol (TRITON X-100 ™) (µg/ml) | 509 | 447 | 579 |
| Ratio t-octylphenoxypolyethoxyethanol (TRITON X-100 ™):HA | ~2.83 | ~2.24 | ~2.88 |

As a comparison, data obtained on H3N2 monovalent bulks manufactured for an H3N2 Fluarix vaccine made using t-octylphenoxypolyethoxyethanol (TRITON X-100™), as disclosed above are presented in Table 7.

TABLE 7

Batch analysis data obtained on H3N2 monovalent bulks

| | A/Uruguay/716/2007 NYMC X-175C Lot N° | | |
|---|---|---|---|
| Parameter | AFLUFDA070 | AFLUFDA071 | AFLUFDA072 |
| HA content SRD Int (µg/ml) | 69 | 82 | 90 |
| Sucrose concentration (µg/mL) | 80 | 89 | 88 |
| Protein (µg/mL) | 172 | 232 | 198 |
| Ovalbumin (ng/mL) | 9 | 12 | 19 |
| Sodium Deoxycholate (µg/mL) | 95 | 105 | 125 |
| Endotoxin (EU/mL) | <0.5 | <0.5 | <0.5 |
| Formaldehyde (µg/mL) | 0.9 | 0.9 | 0.4 |
| Tween (µg/mL) | 391 | 438 | 407 |
| t-octylphenoxypolyethoxyethanol (TRITON X-100 ™) (µg/ml) | 374 | 431 | 474 |
| Viral inactivation | Proved | Proved | Proved |
| Sterility (according to Ph. Eur.) | sterile | sterile | sterile |
| Ratio t-octylphenoxypolyethoxyethanol (TRITON X-100 ™):HA | 5.42 | 5.26 | 5.27 |

Stability data obtained on representative H3N2 monovalent bulks manufactured using the modified seasonal Fluarix process containing t-ctylphenoxypolyethoxyethanol (TRITON X-100™) are presented in Table 9 and Table 10. The ratio of t-octylphenoxypolyethoxyethanol (TRITON X100™)/HA contents pertaining to the lots followed for up to 12 months at 2-8° C. are all close to 3 (see Table 8), and the HA contents are shown to be stable overtime, with comparable values for each time point generated and each lot tested.

Where necessary, t-octylphenoxypolyethoxyethanol (TRITON X-100™) can be detected in the parts per million range by spectrophotometric measurement of the concentration of a t-octylphenoxypolyethoxyethanol (TRITON X-100™)-ammonium-cobalt-thiocyanate complex, see t-octylphenoxypolyethoxyethanol (TRITON X-100™) product information from Sigma and Crabb, N. T. And Persinger, H. E., J. Amer. Oil Chem. Soc., 41, 752-755 (1964) and Greff, R. A. et al., J. Amer. Oil Chem. Soc., 42, 180-185 (1965).

TABLE 8

Ratio t-octylphenoxypolyethoxyethanol (TRITON X-100 ™)/HA contents on the monovalent bulk lots of A/Uruguay/716/2007 NYMC X-175C (H3N2)

| Lot | HA content (µg/ml) Int | t-octylphenoxypolyethoxyethanol (TRITON X-100 ™) (µg/ml) | Ratio t-octylphenoxypolyethoxyethanol (TRITON X-100 ™): HA |
|---|---|---|---|
| AFLUFDA035 | 122 | 455 | 3.73 |
| AFLUFDA036 | 139 | 523 | 3.76 |
| AFLUFDA037 | 131 | 475 | 3.62 |
| AFLUIDA041 | 148 | 415 | 2.80 |
| AFLUIDA042 | 150 | 376 | 2.50 |
| AFLUIDA043 | 156 | 418 | 2.68 |

TABLE 9

Testing of HA content by SRD using NIBSC standards (µg/ml)

| Lot No | 0-day | 2 months | 4 months | 6 months | 9 months | 12 months |
|---|---|---|---|---|---|---|
| AFLUFDA035 | 122 | 134 | 128 | 134 | 128 | 126 |
| AFLUFDA036 | 139 | 156 | 135 | 147 | 142 | 153 |
| AFLUFDA037 | 131 | 138 | 125 | 136 | 135 | 144 |

TABLE 10

Testing of HA content by SRD using CBER standards (µg/ml)

| Lot No | 0-day | 2 months | 4 months | 6 months | 9 months | 12 months |
|---|---|---|---|---|---|---|
| AFLUIDA041 | 152 | 145 | 163 | 166 | 153 | 162 |
| AFLUIDA042 | 162 | 164 | 170 | 170 | 163 | 161 |
| AFLUIDA043 | 157 | 166 | 144 | 176 | 168 | 167 |

Example 4

Preclinical Studies in Mice

In Vivo Potency Mice Methods
Inhibition of Haemagglutination Assay.

Anti-hemagglutinin antibody titers to the a/California/7/2009-X179A influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Heat inactivated sera were previously treated by Kaolin and chicken RBC to remove non-specific inhibitors. After pretreatment, two-fold dilutions of sera were incubated with 4 hemagglutination units of each influenza strain. Chicken red blood cells were then added and the inhibition of agglutination was scored. The titers were expressed as the reciprocal of the highest dilution of serum that completely inhibited hemagglutination. As the first dilution of sera was 1:20, an undetectable level was scored as a titer equal to 10.

In Vivo Potency Test in Mice Immunized with the Non-Adjuvanted A/California/7/2009-X179A Split Vaccine
Experimental Design and Objective
Treatment/Group (Table 11)

Groups of 10 adult female BALB/c mice were vaccinated intraperitoneally with two doses of A/California/7/2009-NYMC X-179A split vaccine in a total volume of 1 ml. Mice were immunized with formulations containing a full Human dose (15 µg HA) or fraction of human dose (3.75, 1.9, 0.46 and 0.115 µg of HA) of A/California/7/2009 split vaccine without addition of t-octylphenoxypolyethoxyethanol (TRITON X-100™) in the bulk t-octylphenoxypolyethoxyethanol (TRITON X-100™)/HA ratio of 1) or with addition of t-octylphenoxypolyethoxyethanol (TRITON X-100™) in the bulk t-octylphenoxypolyethoxyethanol (TRITON X-100™)/HA ratio of 2.83).

Mice were immunized with formulations prepared extemporaneously (TO) or with similar formulations stored 30 days at 30° C. (accelerated stability assumed to mimic a long term stability at 4° C.).

A/California/7/09 split vaccine without addition of octoxynol 10: Lot AFLSFDA048 at 53 µg HA/ml.

A/California/7/09 split vaccine with addition of octoxynol 10: Lot AFLSFDA107 at 180 µg HA/ml.

TABLE 11

| Gr | A/California/7/2009 Antigen/Formulation | (HA/dose) | Dilution step | Other treatment |
|---|---|---|---|---|
| 1 | A/California without t- | 15 | Full HD | Days 0 and 14 |
| 2 | octylphenoxypolyethoxyethanol | 3.75 | ¼ | Days 0 and 14 |
| 3 | (TRITON X-100 ™) (Lot | 1.9 | ⅛ | Days 0 and 14 |
| 4 | AFLSFDA048) | 0.46 | 1/32 | Days 0 and 14 |
| 5 |  | 0.115 | 1/128 | Days 0 and 14 |
| 6 | A/California with t- | 15 | Full HD | Days 0 and 14 |
| 7 | octylphenoxypolyethoxyethanol | 3.75 | ¼ | Days 0 and 14 |
| 8 | (TRITON X-100 ™) (Lot | 1.9 | ⅛ | Days 0 and 14 |
| 9 | AFLSFDA107) | 0.46 | 1/32 | Days 0 and 14 |
| 10 |  | 0.115 | 1/128 | Days 0 and 14 |
| 11 | Dilution buffer A |  |  |  |

Preparation of the Vaccine Formulations

Polyoxyethylene sorbitan monooleate (TWEEN-80™, or POLYSORBATE 80™), t-octylphenoxypolyethoxyethanol (TRITON X-100™) and Thiomersal are added to buffer A (130 mM NaCl, 2.68 mM KCl, 0.49 mM MgCl2. 6H2O, 7.26 mM Na2HPO4.12 H2O, 2.74 mM KH2PO4) in order to reach a final concentration into the vaccine of 115.4 µg/ml of polyoxyethylene sorbitan monooleate (TWEEN-80™, or POLYSORBATE 80™), 15 µg/ml of t-octylphenoxypolyethoxyethanol (TRITON X-100™) and of 10 µg/ml of Thiomersal. The quantities used are calculated taking into account the quantities already present in the strains. The premix are mixed 15 to 45 minutes on an orbital shaking table at room temperature before the addition of 15 µg of A/California split vaccines. After the addition of the split vaccines, the formulations are mixed 15 to 45 min on an orbital shaking table at room temperature.

Part of the full dose formulations are extemporaneously diluted ¼, ⅛, ½₂ and ½₂₈-fold in the same buffer A (see above) by serial dilutions. The full dose and the dilutions are injected within the hour following the end of their preparation.

Another part of the full dose formulation is incubated 30 days at 30° C. and extemporaneously diluted and injected.

Read-Outs

The humoral immune response to vaccination was measured 14 days after the second immunization (Day 28), on 10 mice/group. Serum samples were tested by the hemagglutination inhibition assay (HI).

Results

Humoral Immune Responses

The results are shown in FIGS. 4 and 5.

Two immunizations are required in mice immunized with the non-adjuvanted vaccine in order to induce HI titers >40.

With the process without addition of t-octylphenoxypolyethoxyethanol (TRITON X-100™) (FIG. 4), only the mice immunised with the full human dose (15 μg HA) of the non-adjuvanted vaccine stored 30 days at 30° C. showed similar immune response compared to the mice immunised with the non-adjuvanted vaccine prepared extemporaneously.

With the addition of t-octylphenoxypolyethoxyethanol (TRITON X-100™) in the process (FIG. 5), similar immune responses were observed between mice immunized with the full human dose (15 μg HA) and ¼ human dose of the non-adjuvanted vaccine stored 30 days at 30° C. and mice immunized with the non-adjuvanted vaccine prepared extemporaneously.

Conclusion

Compared to the immune response induced in mice immunised with the non-adjuvanted vaccine prepared extemporaneously, the non-adjuvanted vaccine stored 30 days at 30° C. showed higher stability with the addition of t-octylphenoxypolyethoxyethanol (TRITON X-100™) compared to the non-adjuvanted vaccine formulated without addition of t-octylphenoxypolyethoxyethanol (TRITON X-100™).

In Vivo Potency Test in Mice Immunized with AS03A-Adjuvanted A/California/7/2009-X179A Split Vaccine Experimental Design and Objective Treatment/Group (Table 12)

Groups of 10 adult female BALB/c mice were immunised intraperitoneally with two doses of A/California/7/2009-NYMC X-179A split vaccine adjuvanted with ASO3$_A$ in a total volume of 1 ml. A Human dose (HD) was considered at 15 μg HA and containing 11.8 mg alpha-tocopherol (Vitamin E).

Mice were immunised with a half Human dose of adjuvanted vaccine and 2-fold or 4-fold step dilution of vaccine (7.5, 3.75, 1.9, 0.46 and 0.115 μg HA) without the addition of t-octylphenoxypolyethoxyethanol (TRITON X-100™) in the bulk (t-octylphenoxypolyethoxyethanol (TRITON X-100™)/HA ratio of 1) or with the addition of t-octylphenoxypolyethoxyethanol (TRITON X-100™) in the bulk (t-octylphenoxypolyethoxyethanol (TRITON X-100™)/HA ratio of 2.83).

Mice were immunized with formulations prepared extemporaneously (T0) or with similar formulations stored 30 days at 30° C.

Split A/California virus antigen without additional octoxynol: Lot AFLSFDA048-53 μgHA/ml Split A/California virus antigen containing additional octoxynol 10: Lot AFLSFDA107-180 μgHA/ml

TABLE 12

| Gr | Antigen/Formulation | A/California/ 7/2009 (Conc HA/dose) | Dilution step | Other treatment |
|---|---|---|---|---|
|  | A/California without t- | 15 μg | Full HD |  |
| 1 | octylphenoxypoly- | 7.5 μg | ½ | Days 0 and 14 |
| 2 | ethoxyethanol | 3.75 μg | ¼ | Days 0 and 14 |
| 3 | (TRITON X-100 ™) - | 1.9 μg | ⅛ | Days 0 and 14 |
| 4 | AS03A | 0.46 μg | ½₂ | Days 0 and 14 |
| 5 | (Lot AFLSFDA048) | 0.115 μg | ½₂₈ | Days 0 and 14 |
|  | A/California with | 15 μg | Full HD |  |
| 6 | octylphenoxypoly- | 7.5 μg | ½ | Days 0 and 14 |
| 7 | ethoxyethanol | 3.75 μg | ¼ | Days 0 and 14 |
| 8 | (TRITON X-100 ™) - | 1.9 μg | ⅛ | Days 0 and 14 |
| 9 | AS03A | 0.46 μg | ½₂ | Days 0 and 14 |
| 10 | (Lot AFLSFDA107) | 0.115 μg | ½₂₈ |  |
| 11 | Dilution buffer A |  |  |  |

Data obtained with full human dose and ½ human dose of AS03A-adjuvanted A/California/7/09 vaccine were not included due to high level of mortality (>50%) in mice immunised by intraperitoneal route.

Preparation of the Vaccine Formulations.

Polyoxyethylene sorbitan monooleate (TWEEN-80™ or POLYSORBATE 80™), t-octylphenoxypolyethoxyethanol (TRITON X-100™) and Thiomersal are added to buffer A (130 mM NaCl, 2.68 mM KCl, 0.49 mM MgCl2. 6H2O, 7.26 mM Na2HPO4.12 H2O, 2.74 mM KH2PO4) in order to reach a final concentration into the vaccine of 115.4 μg/ml of polyoxyethylene sorbitan monooleate (TWEEN-80™ or POLYSORBATE 80™), 15 μg/ml of t-octylphenoxypolyethoxyethanol (TRITON X-100™) and of 10 μg/ml of Thiomersal. The quantities used are calculated to take into account the quantities already present in the strains. The premix are mixed 15 to 45 minutes on an orbital shaking table at room temperature before the addition of 15 μg of A/California split vaccines. After the addition of the split vaccines, the formulations are mixed for 15 to 45 min on an orbital shaking table at room temperature. The oil-in-water emulsion is then added in order to reach a final concentration of 10.69 mg squalene, 11.86 mg alpha-tocopherol and 4.86 mg polyoxyethylene sorbitan monooleate (TWEEN-80™ or POLYSORBATE 80™) per ml. The vaccine is mixed 15 to 45 min on an orbital shaking table at room temperature.

Part of the full dose formulations are extemporaneously diluted 1/2, 1/4, 1/8, 1/32 and 1/128-fold in buffer A by serial dilutions. The full dose and the dilutions are injected within the hour following the end of their preparation.

Another part of the full dose formulations is incubated 30 days at 30° C. and extemporaneaously diluted and injected.

Read-Outs

The humoral immune response to vaccination was measured 14 days after the first (Day 14) and the second immunization (Day 28) on 10 mice/group. Serum samples were tested by the inhibition hemagglutination assay (HI).

Results

Humoral Immune Responses

The results are shown in FIGS. 6 and 7, 14 days after the first dose, and in FIGS. 8 and 9, 14 days after the second dose.

HI titers above 40 were observed after one dose of AS03A-adjuvanted vaccine prepared extemporaneously. After one dose of AS03A-adjuvanted vaccine, and whether t-octylphenoxypolyethoxyethanol (TRITON X-100™) was present (FIG. 7) or not (FIG. 6), significant lower HI titers were observed after storage 30 days at 30° C. compared to the immune response induced in mice immunized with the AS03A-adjuvanted vaccine prepared extemporaneously.

Higher HI titres were observed in mice immunized with two doses of AS03A-adjuvanted vaccines compared to the immune response induced in mice immunized with a single dose of AS03A-adjuvanted vaccine (FIGS. 8 and 9).

After administration of two doses of AS03A-adjuvanted vaccines prepared without the addition of t-ocylphenoxypolyethoxyethanol (TRITON X-100™) (FIG. 8), lower HI titers were observed in mice immunized with the vaccine stored 30 days at 30° C. compared to mice immunized with the vaccine prepared extemporaneously.

With the addition of t-octylphenoxypolyethoxyethanol (TRITON X-100™) in the process (FIG. 9), similar immune responses were observed in mice immunized with the adjuvanted vaccine stored 30 days at 30° C. and the adjuvanted vaccine prepared extemporaneously.

Conclusion

Compared to the immune response induced in mice immunized with the adjuvanted vaccine prepared extemporaneously, the adjuvanted vaccine stored 30 days at 30° C. showed higher stability with the addition of t-octylphenoxypolyethoxyethanol (TRITON X-100™) compared to the adjuvanted vaccine prepared without the addition of t-octylphenoxypolyethoxyethanol (TRITON X-100™).

General Conclusion

Vaccination of mice with non-adjuvanted or AS03A-adjuvanted A/California/7/09 split vaccines produced with a process containing higher concentration of t-octylphenoxypolyethoxyethanol (TRITON X-100™) resulted in higher humoral immune responses (HI titers) compared to vaccines prepared without the addition of t-octylphenoxypolyethoxyethanol (TRITON X-100™). These data demonstrated an improved stability of the split vaccine, adjuvanted or not with AS03A, when this vaccine is prepared with an addition of t-octylphenoxypolyethoxyethanol (TRITON X-100™) during the process.

Example 5

A Phase III, Double-Blind, Randomized, Study in Adults Aged Between 18 and 60 Years Introduction and Study Design A phase III, double-blind, randomized, study was conducted in adults aged between 18 and 60 years to assess the immunological non-inferiority of two manufacturing processes of the A/California/7/2009 (H1N1)v-like antigen adjuvanted with AS03A.

Four parallel groups (1:1:1:1) with approximately 300 subjects in total receiving the following vaccines IM:
D-INI-1D group: 75 subjects receiving one dose of initial process-manufactured Flu D-PAN H1N1 candidate vaccine adjuvanted with AS03A
D-INI-2D group: 75 subjects receiving two doses of initial process-manufactured Flu D-PAN H1N1 candidate vaccine adjuvanted with AS03A
D-NEW-1D: 75 subjects receiving one dose of new process-manufactured Flu D-PAN H1N1 candidate vaccine adjuvanted with AS03A
D-NEW-2D: 75 subjects receiving two doses of new process-manufactured Flu D-PAN H1N1 candidate vaccine adjuvanted with AS03A Schedule: One or two intramuscular (IM) injections, only one for the two groups 1 (Day 0) or two for the two groups 2 (Day 0 and Day 21), blood sample collection at day 0, day 21, day 42, day 182 and day 364 postvaccination.

Study Objectives

Immunological non-inferiority (in terms of vaccine-homologous virus H1N1 HI antibody GMTs—Haemagglutination Inhibition (HI) antibodies) of the new process-manufactured A/California/7/2009 (H1N1)v-like antigen adjuvanted with AS03A was compared to the initial process-manufactured A/California/7/2009 (H1N1)v-like antigen adjuvanted with AS03A, 21 days after first vaccination in healthy subjects aged 18 to 60 years. Non-inferiority is considered to be reached if the upper limit of the two-sided 95% CI for the ratio of GMT between the initial process-manufactured vaccine and (over) new process-manufactured vaccine is less than or equal to 2 in terms of HI antibody titre against A/California/7/2009 (H1N1)v-like. Geometric mean titres (GMTs) of HI antibody titres 21 days after first dose of vaccine (Day 21) and 21 days after second vaccination have also been measured. Additional parameters such as seroconversion rates (SCR—defined as the percentage of vaccinees who have either a prevaccination titre <1:10 and a post-vaccination titre ≥1:40 or a pre-vaccination titre ≥1:10 and at least a four-fold increase in post-vaccination titre), Seroconversion factors (SCF—defined as the fold increase in serum HI GMTs post-vaccination compared to pre-vaccination), seroprotection rates (SPR—defined as the percentage of vaccinees with a serum HI titre ≥1:40 that usually is accepted as indicating protection), and neutralizing antibodies are also reported below.

Antigen Preparation

The only difference between the two processes D-INI and D-NEW is the addition of t-octylphenoxypolyethoxyethanol (TRITON X-100™), immediately after splitting of the virus. This helps preventing aggregation of the antigen and loss of antigen during the final sterile filtration step. FIG. 1 shows an overview of the method of preparation of the split, inactivated H1N1v bulk preparation for D-INI (left column) and D-NEW (middle column)

Basically, the manufacturing process of the bulks can be divided in four main parts and is largely based on the process described in Example 5a of WO 02/097072 (U.S. Pat. No. 7,316,813B2) with the omission of the addition of alpha-tocopherol succinate stabiliser:
1. Propagation of the working seed in fertilized hen's eggs, harvesting and pooling of infected allantoic fluids so as to obtain the "crude whole virus bulk" (step 1).
2. Purification of each virus strain leading to the "purified whole virus bulk" (steps 2-6).
3. Splitting of the purified monovalent whole virus bulk with sodium deoxycholate resulting in the "purified split virus bulk" (steps 7-8/1).
4. Inactivation of the purified monovalent split virus bulk in two steps by incubation with sodium deoxycholate and with formaldehyde, followed by ultrafiltration and sterile filtration, in order to obtain the "purified inactivated split virus bulk", or "Bulk" (steps 8/2-9).

The purified split virus bulk (fraction 7/2 in FIG. 1) of the D-NEW process is then subjected to the following treatment. Prior to filtration, t-octylphenoxypolyethoxyethanol (TRI- TON X-100™) is added (so as to reach 0.25% final concentration in the filtrate). Fraction 7/2 is gradually filtered down to a 0.45 µm or higher filter membrane, followed by a second membrane filtration step with a pore size of 0.45 µm or lower, with the aim of removing bioburden. The filtrate is then briefly sonicated and filtered through a membrane of pore size 0.45 µm or below. At the end of the filtration, the filters are rinsed with phosphate buffer containing 0.025% Tween-80. As a result of the filtration and rinsing, the final volume of the filtrate is 5-fold the original fraction 7/2 volume.

Thiomersal is added to the formulation (in both processes), present in 10-doses presentation, at a concentration of 5 μg per dose.

Vaccine Composition

The HA content per dose of vaccine has been fixed at 3.75 μg per 0.5 ml dose and the vaccine after reconstitution contains some excipients such as polyoxyethylene sorbitan monooleate (TWEEN-80™, or POLYSORBATE 80™) and t-octylphenoxypolyethoxyethanol (TRITON X-100™) to an amount of ≥28.75 μg and 22.5 μg per 0.5 ml dose respectively. AS03A adjuvant is an oil-in-water emulsion adjuvant system containing 11.86 mg tocopherol, 10.69 mg squalene and 4.86 mg polyoxyethylene sorbitan monooleate (TWEEN-80™, or POLYSORBATE 80™) per 0.5 ml vaccine dose (WO2006/100109). The reconstituted vaccine is made by mixing the adjuvant 0/W emulsion with the antigen suspension. The composition of the reconstituted vaccine also contains 5 μg thiomersal per 0.5 ml dose.

The antigen lots used in the study were:

Lot no for H1N1 (new process D-NEW)=DFLSA014A; lot no for the adjuvant AA03A209C; the t-octylphenoxypolyethoxyethanol (TRITON X-100™) content is 22.5 μg/0.25 mL of antigen suspension Lot no for H1N1 (initial process D-INI)=DFLSA013A; lot no for the adjuvant AA03A209C; the t-octylphenoxypolyethoxyethanol (TRITON X-100™) content is 3.75 μg/0.25 mL (ratio of 1:1 to the HA content) of antigen suspension The content in Tween-80 for the H1N1 antigen suspension is >=28.75 μg/0.25 mL of antigen suspension (target formulation of 115 μg/ml) for both antigen suspensions but does not exceed 55 μg/0.25 mL (220 μg/mL). The composition of the antigen suspension is in Table 13.

TABLE 13

Composition of inactivated split virion H1N1 antigen component

| Ingredients | Quantity per 0.25 ml - DFLSA013A (initial process) | Quantity per 0.25 ml - DFLS014A (adapted process) | Unit |
|---|---|---|---|
| Purified antigen fractions of inactivated split virion A/California/7/2009 (H1N1)v NYMC X-179A | 3.75 | 3.75 | μg HA |
| Polyoxyethylene sorbitan monooleate (TWEEN-80 ™, or POLYSORBATE 80 ™) | ≥28.75 | ≥28.75 | μg |
| t-octylphenoxypolyethoxyethanol (TRITON X-100 ™) | 3.75 | 22.5 | μg |
| Sodium chloride | 1.92 | 1.92 | mg |
| Disodium phosphate | 0.26 | 0.26 | mg |
| Potassium dihydrogen phosphate | 0.094 | 0.094 | mg |
| Potassium chloride | 0.050 | 0.050 | mg |
| Magnesium chloride | 0.012 | 0.012 | mg |
| Thiomersal | 5 | 5 | μg |
| Water for injections q.s. ad. | 0.25 | 0.25 | ml |

Immunogenicity Results—Humoral Immune Response

Non-Inferiority of the New Process-Manufactured A/California/7/2009 (H1N1)v-Like Antigen Adjuvanted with AS03A Vaccine Compared to the Initial Process-Manufactured A/California/7/2009 (H1N1)v-Like Antigen Adjuvanted with AS03A Vaccine (GMT).

The new process-manufactured A/California/7/2009 (H1N1)v-like antigen adjuvanted with AS03A vaccine was shown to be non-inferior to the initial process-manufactured A/California/7/2009 (H1N1)v-like antigen adjuvanted with AS03A vaccine, both in terms of GMT ratios at Day 21 (Table 14) and in terms of seroconversion rate difference at Day 21 (Table 15).

TABLE 14

Adjusted GMT ratios between D-INI and D-NEW for HI antibodies at Day 21 (ATP cohort for immunogenicity)

| Group description | N | Adjusted GMT | Group description | N | Adjusted GMT | Adjusted GMT ratio: Ratio order | Adjusted GMT ratio: Value | 95% CI: LL | 95% CI: UL |
|---|---|---|---|---|---|---|---|---|---|
| D-INI | 144 | 437.9 | D-NEW | 146 | 392.2 | D-INI/D-NEW | 1.12 | 0.89 | 1.40 |

1. D-NEW = Subjects receiving the new process-manufactured Flu D-PAN H1N1 vaccine with adjuvant 2. D-INI = Subjects receiving the initial process-manufactured Flu D-PAN H1N1 vaccine with adjuvant 3. Adjusted GMT = geometric mean antibody titre adjusted for baseline titre 4. N = Number of subjects with both pre- and post-vaccination results available 5. 95% CI = 95% confidence interval for the adjusted GMT ratio (Ancova model: adjustment for baseline titre-pooled variance); LL = lower limit, UL = upper limit

TABLE 15

The difference between D-INI and D-NEW seroconversion rate at Day 21
(ATP cohort for immunogenicity)

| Antibody | Pre-vaccination status | D-INI N | D-INI n | D-INI % | D-NEW N | D-NEW n | D-NEW % | Difference in vaccine response rate (D-INI minus D-NEW) % | 95% CI LL | 95% CI UL |
|---|---|---|---|---|---|---|---|---|---|---|
| Flu A/CAL/7/09.HA1 Ab (1/DIL) | Total | 144 | 138 | 95.8 | 146 | 141 | 96.6 | −0.74 | −5.82 | 4.16 |

1. D-NEW = Subjects receiving the new process-manufactured Flu D-PAN H1N1 vaccine with adjuvant
2. D-INI = Subjects receiving the initial process-manufactured Flu D-PAN H1N1 vaccine with adjuvant
3. N = number of subjects with pre- and post-vaccination results available
4. n/% = number/percentage of subjects with a vaccine response
5. 95% CI = Standardized asymptotic 95% confidence interval; LL = lower limit, UL = upper limit HI Geometric Mean Titres (GMT)

The GMT's for HI antibodies with 95% CI are shown in Table 16. At Day 0, seropositivity rates were 43.2% to 47.2%. Before vaccination, GMT values were low and ranged between 9.6 and 10.2. At Day 21, seropositivity rates increased to 100% in both groups (D-INI and D-NEW). The amplitude of the observed HI response was similar in both groups (GMTs of 388.8 for the D-NEW group versus 441.8 for the D-INI group).

TABLE 16

Seropositivity rates and GMTs for HI antibodies at Day 0 and Day 21
(ATP cohort for immunogenicity).

| Antibody | Group | Timing | N | >= 10 1/D1L n | >= 10 1/D1L % | 95% CI LL | 95% CI UL | GMT value | 95% CI LL | 95% CI UL | Min | Max |
|---|---|---|---|---|---|---|---|---|---|---|---|---|
| Flu A/CAL/7/09.HA1 Ab | D-NEW | PRE | 146 | 63 | 43.2 | 35.0 | 51.6 | 9.6 | 8.3 | 11.2 | <10.0 | 640.0 |
| | | PI(D21) | 146 | 146 | 100 | 97.5 | 100 | 388.8 | 331.3 | 456.3 | 40.0 | 2560.0 |
| | D-INI | PRE | 144 | 68 | 47.2 | 38.9 | 55.7 | 10.2 | 8.7 | 12.0 | <10.0 | 640.0 |
| | | PI(D21) | 144 | 144 | 100 | 97.5 | 100 | 441.8 | 372.4 | 524.0 | 20.0 | 5120.0 |

1. D-NEW = Subjects receiving the new process-manufactured Flu D-PAN H1N1 vaccine with adjuvant
2. D-INI = Subjects receiving the initial process-manufactured Flu D-PAN H1N1 vaccine with adjuvant
3. GMT = geometric mean antibody titre calculated on all subjects
4. N = number of subjects with available results
5. n/% = number/percentage of subjects with titre within the specified range
6. 95% CI = 95% confidence interval; LL = Lower Limit, UL = Upper Limit
7. MIN/MAX = Minimum/Maximum
8. PRE = visit 1 Day 0
9. PI(D21) = visit 2 Day 21

Seroprotection Rates, Seroconversion Rates and Seroconversion Factors of Anti-HI Ab Titres Results are presented in Table 17 for seroprotection rates (SPR), Table 18 for seroconversion rates (SCR) and Table 19 for seroconversion factors (SCF).

SPR were shown to be within the same range and met CHMP (mean>70) in both groups. SCR induced by the new process-manufactured Flu D-PAN H1N1 vaccine and the initial process-manufactured Flu D-PAN H1N1 vaccine were within the same range and both met CHMP criteria (mean>40). For both groups SCF were within the same range and were above the CHMP criteria (>2.5).

TABLE 17

Seroprotection rates (SPR) for HI antibodies at Day 0 and Day 21
(ATP cohort for immunogenicity)

| Strain | Group | Timing | N | n | SPR % | 95% CI LL | 95% CI UL |
|---|---|---|---|---|---|---|---|
| Flu A/CAL/7/09.HA1 Ab | D-NEW | PRE | 146 | 17 | 11.6 | 6.9 | 18.0 |
| | | PI(D21) | 146 | 146 | 100 | 97.5 | 100 |
| | D-INI | PRE | 144 | 22 | 15.3 | 9.8 | 22.2 |
| | | PI(D21) | 144 | 142 | 98.6 | 95.1 | 99.8 |

1. D-NEW = Subjects receiving the new process-manufactured Flu D-PAN H1N1 vaccine with adjuvant
2. D-INI = Subjects receiving the initial process-manufactured Flu D-PAN H1N1 vaccine with adjuvant

TABLE 17-continued

Seroprotection rates (SPR) for HI antibodies at Day 0 and Day 21
(ATP cohort for immunogenicity)

| Strain | Group | Timing | N | n | % | SPR 95% CI LL | UL |
|---|---|---|---|---|---|---|---|

3. N = Number of subjects with available results
4. n/% = Number/percentage of seroprotected subjects (HI titer >= 40 1/DIL)
5. 95% CI = 95% confidence interval, LL = Lower Limit, UL = Upper Limit
6. PRE = visit 1 Day 0
7. PI(D21) = visit 2 Day 21

TABLE 18

Seroconversion rate (SCR) for HI antibodies at Day 21
(ATP cohort for immunogenicity)

| Strain | Group | Timing | N | n | % | SCR 95% CI LL | UL |
|---|---|---|---|---|---|---|---|
| Flu A/CAL/7/ 09.HA1 Ab | D-NEW | PI(D21) | 146 | 141 | 96.6 | 92.2 | 98.9 |
| | D-INI | PI(D21) | 144 | 138 | 95.8 | 91.2 | 98.5 |

1. D-NEW = Subjects receiving the new process-manufactured Flu D-PAN H1N1 vaccine with adjuvant
2. D-INI = Subjects receiving the initial process-manufactured Flu D-PAN H1N1 vaccine with adjuvant
3. N = Number of subjects with pre- and post-vaccination results available
4. n/% = Number/percentage of seroconverted subjects
5. 95% CI = 95% confidence interval, LL = Lower Limit, UL = Upper Limit
6. PI(D21) = visit 2 Day 21

TABLE 19

Seroconversion factor (SCF) for HI antibody titer at Day 21
(ATP cohort for immunogenicity)

| Vaccine strain | Group | Timing | N | SCF Value | 95% CI LL | UL |
|---|---|---|---|---|---|---|
| Flu A/CAL/7/ 09.HA1 Ab (1/DIL) | D-NEW | PI(D21) | 146 | 40.4 | 33.3 | 49.1 |
| | D-INI | PI(D21) | 144 | 43.4 | 35.9 | 52.4 |

1. D-NEW = Subjects receiving the new process-manufactured Flu D-PAN H1N1 vaccine with adjuvant
2. D-INI = Subjects receiving the initial process-manufactured Flu D-PAN H1N1 vaccine with adjuvant
3. N = Number of subjects with pre- and post-vaccination results available
4. SCF = Seroconversion Factor or geometric mean ratio (mean[log10(POST/PRE)])
5. 95% CI = 95% confidence interval, LL = Lower Limit, UL = Upper Limit
6. PI(D21) = visit 2 Day 21

Immunological Response Per Age Strata

Results are presented in Table 20 for seropositivity, GMT, seroprotection rates, seroconversion rates and for seroconversion factors, overall and by age stratum (18-40 years and 41-60 years).

Overall as per age strata, at Day 21, immune responses in subjects from D-INI and D-NEW groups both exceeded all CHMP regulatory acceptance criteria for influenza vaccines in adults. All tested parameters can be considered as similar between both groups.

TABLE 20

H1N1 HI antibodies against A/California/7/2009 (H1N1)v-like strain by age strata and overall.

| | | ≥10 1/DIL | | | GMT | | | SPR | | | SCR[#] | | | SCF | | |
|---|---|---|---|---|---|---|---|---|---|---|---|---|---|---|---|---|
| | | | 95% CI | | | 95% CI | | | 95% CI | | | 95% CI | | | 95% CI | |
| Timing | N | % | LL | UL | value | LL | UL | % | LL | UL | % | LL | UL | value | LL | UL |
| Overall D-NEW group | | | | | | | | | | | | | | | | |
| PRE | 146 | 43.2 | 35.0 | 51.6 | 9.6 | 8.3 | 11.2 | 11.6 | 6.9 | 18.0 | — | — | — | — | — | — |
| PI(D21) | 146 | 100 | 97.5 | 100 | 388.8 | 331.3 | 456.3 | 100 | 97.5 | 100 | 96.6 | 92.2 | 98.9 | 40.4 | 33.3 | 49.1 |
| 18-40 years stratum D-NEW group | | | | | | | | | | | | | | | | |
| PRE | 74 | 45.9 | 34.3 | 57.9 | 10.3 | 8.2 | 12.9 | 12.2 | 5.7 | 21.8 | — | — | — | — | — | — |
| PI(D21) | 74 | 100 | 95.1 | 100 | 456.8 | 373.4 | 558.8 | 100 | 95.1 | 100 | 97.3 | 90.6 | 99.7 | 44.4 | 34.6 | 57.1 |
| 41-60 years stratum D-NEW group | | | | | | | | | | | | | | | | |
| PRE | 72 | 40.3 | 28.9 | 52.5 | 9.0 | 7.4 | 11.0 | 11.1 | 4.9 | 20.7 | — | — | — | — | — | — |
| PI(D21) | 72 | 100 | 95.0 | 100 | 329.5 | 256.9 | 422.5 | 100 | 95.0 | 100 | 95.8 | 88.3 | 99.1 | 36.6 | 27.0 | 49.7 |
| Overall D-INI group | | | | | | | | | | | | | | | | |
| PRE | 144 | 47.2 | 38.9 | 55.7 | 10.2 | 8.7 | 12.0 | 15.3 | 9.8 | 22.2 | — | — | — | — | — | — |
| PI(D21) | 144 | 100 | 97.5 | 100 | 441.8 | 372.4 | 524.0 | 98.6 | 95.1 | 99.8 | 95.8 | 91.2 | 98.5 | 43.4 | 35.9 | 52.4 |
| 18-40 years stratum D-INI group | | | | | | | | | | | | | | | | |
| PRE | 74 | 45.9 | 34.3 | 57.9 | 10.1 | 8.0 | 12.9 | 16.2 | 8.7 | 26.6 | — | — | — | — | — | — |
| PI(D21) | 74 | 100 | 95.1 | 100 | 564.0 | 446.9 | 711.8 | 100 | 95.1 | 100 | 97.3 | 90.6 | 99.7 | 55.6 | 42.9 | 72.1 |
| 41-60 years stratum D-INI group | | | | | | | | | | | | | | | | |
| PRE | 70 | 48.6 | 36.4 | 60.8 | 10.2 | 8.2 | 12.8 | 14.3 | 7.1 | 24.7 | — | — | — | — | — | — |
| PI(D21) | 70 | 100 | 94.9 | 100 | 341.2 | 267.9 | 434.6 | 97.1 | 90.1 | 99.7 | 94.3 | 86.0 | 98.4 | 33.3 | 25.4 | 43.6 |

GMT = Geometric Mean Titer;
SPR = Seroprotection rate: percentage of subjects with antibody titer ≥ 1:40;
SCR = Seroconversion rate: percentage of subjects with antibody titer ≥ 40 1/DIL after vaccination for initially seronegative subjects, or ≥4 fold the pre-vaccination antibody titer for initially seropositive subjects;
SCF = Seroconversion factor: fold increase in GMTs post-vaccination compared with pre-vaccination;
PRE = pre-vaccination;

TABLE 20-continued

H1N1 HI antibodies against A/California/7/2009 (H1N1)v-like strain by age strata and overall.

| | | ≥10 1/DIL | | | GMT | | | SPR | | | SCR# | | | SCF | |
|---|---|---|---|---|---|---|---|---|---|---|---|---|---|---|---|
| | | | 95% CI | | | 95% CI | | | 95% CI | | | 95% CI | | | 95% CI |
| Timing | N | % | LL | UL | value | LL | UL | % | LL | UL | % | LL | UL | value | LL | UL |

PI(D21) = post-vaccination I at Day 21;
LL = Lower Limit;
UL = Upper Limit;
N = number of subjects with available results.

Reactogenicity Results

Solicited local symptoms were reported at similar frequencies in the D-NEW and D-INI groups. Pain at injection site was the most frequently reported symptom, while swelling and redness were observed at lower frequencies in both groups. Grade 3 solicited local symptoms were infrequent and similar in both groups.

With the exception of shivering which was reported with a higher frequency in the D-INI (27.5%) compared to the D-NEW (18.8%) group, solicited general symptoms were reported at equivalent frequencies in both groups. Grade 3 related solicited general symptoms were infrequent and similar in both groups (between 0% and 2.0%).

Conclusions

Immunogenicity Conclusions

The immunological non-inferiority objective (in terms of GMTs and SCRs) of the new process-manufactured A/California/7/2009 (H1N1)v-like antigen adjuvanted with AS03A compared to the initial process-manufactured A/California/7/2009 (H1N1)v-like antigen adjuvanted with AS03A, 21 days after first vaccination in healthy subjects aged 18 to 60 years were both reached.

The HI humoral immune response observed 21 days following the first administration of the influenza pandemic vaccine at 3.75 µg HA antigen met and exceeded all EMEA/CHMP regulatory acceptance criteria in terms of SCR, SPR and SCF in all age strata and in both groups, having received one dose of either the initial or the new process-manufactured vaccines.

Furthermore the EMEA/CHMP acceptance criteria in terms of SCR, SPR and SCF are also met and exceeded 21 days after the second vaccination for both vaccines.

Safety Conclusions

The reactogenicity profiles were comparable in both groups. The most frequent solicited AEs were pain at injection site, fatigue, muscles aches and headaches. The individual values of all reactogenicity parameters are similar for D-New and D-Ini vaccines.

OVERALL CONCLUSION

The H1N1 candidate vaccine manufactured with the new process and adjuvanted with AS03A elicits an immune response against the A/California/7/2009 (H1N1)v-like strain in adults that is non inferior to the immune response induced by the vaccine antigen manufactured according to the initial process. Both vaccines demonstrated an acceptable reactogenicity profile, no safety concerns were raised.

We claim:

1. A process for producing a split monovalent influenza virus preparation or subunit influenza preparation comprising the steps of: (i) providing a whole virus preparation; (ii) splitting the whole virus preparation in the presence of a first detergent, wherein the first detergent is not t-octylphenoxypolyethoxyethanol, thereby producing a split virus preparation; (iii) adding t-octylphenoxypolyethoxyethanol to the split virus preparation, wherein t-octylphenoxypolyethoxyethanol is present in an amount of 0.1-0.4% (w/v); and (iv) filtering the split virus preparation in the presence of t-octylphenoxypolyethoxyethanol.

2. The process of claim 1 wherein the filtering step is performed using one or more filter membranes, wherein at least one filter membrane is sterile grade.

3. The process of claim 1 wherein t-octylphenoxypolyethoxyethanol is present in an amount sufficient to increase HA yield in the filtered split virus preparation as compared to HA yield from a process in which t-octylphenoxypolyethoxyethanol is not added to the split virus preparation.

4. The process of claim 1 wherein t-octylphenoxypolyethoxyethanol is present in an amount of 0.25% w/v.

5. The process of claim 1 further comprising the step of inactivating the split influenza virus preparation.

6. The process of claim 5 wherein the inactivation step is performed after step (iii) and before step (iv).

7. The process of claim 5 wherein the inactivation step is performed after step (iv).

8. The process of claim 1 comprising a second step of filtering the split influenza virus preparation in addition to the filtration step of step (iv).

9. The process of claim 1 wherein the first detergent is selected from the group consisting of: cetyl trimethyl ammonium bromide (CTAB), laurylsulfate, taurodeoxycholate, polyoxyethylene sorbitan monooleate and sodium deoxycholate.

10. The process of claim 1 further comprising the step of ultracentrifuging the split influenza virus preparation.

11. The process of claim 1 further comprising the step of clarifying the whole virus preparation.

12. The process of claim 1 further comprising the step of ultrafiltering the whole virus preparation.

13. The process of claim 1 wherein the split influenza virus preparation is derived from a pandemic strain.

14. The process of claim 1 wherein the split influenza virus preparation is derived from an interpandemic strain.

15. The process of claim 1 wherein the first detergent is sodium deoxycholate.

16. The process of claim 1 wherein steps (iii) and (iv) are performed simultaneously.

17. The process of claim 1 wherein the HA concentration in the filtered split influenza virus preparation or subunit preparation is more than 50% greater than the HA concentration from a process in which t-octylphenoxypolyethoxyethanol is not added to the split virus preparation prior to filtration.

18. The process of claim 1 wherein the HA concentration in the filtered split influenza virus preparation or subunit preparation is more than 50% greater than the HA concentration from a process in which polyoxyethylene sorbitan monooleate is added to step (ii) and wherein t-octylphenoxypolyethoxyethanol is not added to the split virus preparation prior to filtration.

* * * * *

UNITED STATES PATENT AND TRADEMARK OFFICE
CERTIFICATE OF CORRECTION

PATENT NO.        : 9,636,394 B2                                    Page 1 of 1
APPLICATION NO.   : 13/503859
DATED             : May 2, 2017
INVENTOR(S)       : D'Hondt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 254 days.

Signed and Sealed this
Twenty-fifth Day of September, 2018

Andrei Iancu
*Director of the United States Patent and Trademark Office*